(12) United States Patent
Wu

(10) Patent No.: US 11,430,347 B2
(45) Date of Patent: Aug. 30, 2022

(54) PROVIDING DIET ASSISTANCE IN A SESSION

(71) Applicant: Microsoft Technology Licensing, LLC, Redmond, WA (US)

(72) Inventor: Xianchao Wu, Tokyo (JP)

(73) Assignee: Microsoft Technology Licensing, LLC, Redmond, WA (US)

( * ) Notice: Subject to any disclaimer, the term of this patent is extended or adjusted under 35 U.S.C. 154(b) by 169 days.

(21) Appl. No.: 16/637,057

(22) PCT Filed: Sep. 18, 2017

(86) PCT No.: PCT/CN2017/102141
§ 371 (c)(1),
(2) Date: Feb. 6, 2020

(87) PCT Pub. No.: WO2019/051847
PCT Pub. Date: Mar. 21, 2019

(65) Prior Publication Data
US 2020/0242964 A1    Jul. 30, 2020

(51) Int. Cl.
*G09B 19/00*    (2006.01)
*G16H 20/60*    (2018.01)
(Continued)

(52) U.S. Cl.
CPC ... *G09B 19/0092* (2013.01); *G06F 16/24578* (2019.01); *G06F 16/90332* (2019.01);
(Continued)

(58) Field of Classification Search
CPC .......................... G09B 19/0092; G16H 20/60
See application file for complete search history.

(56) References Cited

U.S. PATENT DOCUMENTS

2009/0075242 A1* 3/2009 Schwarzberg ..... G09B 19/0092
434/127
2009/0275002 A1* 11/2009 Hoggle .................. G16H 20/60
707/999.1
(Continued)

FOREIGN PATENT DOCUMENTS

CN        105068661 A    11/2015
CN        105335398 A    2/2016
(Continued)

OTHER PUBLICATIONS

"International Search Report and Written Opinion issued in PCT Application No. PCT/CN2017/102141", dated Jun. 27, 2018, 9 Pages.

*Primary Examiner* — Peter R Egloff
(74) *Attorney, Agent, or Firm* — Schwegman Lundberg & Woessner, P.A.

(57) ABSTRACT

The present disclosure provides method and apparatus for providing diet assistance to a user in a session. At least one message may be received in the session, the session being between the user and an electronic conversational agent. A diet intention associated with the user may be deduced based on the session and the at least one message. Diet information may be extracted from the at least one message. A diet requirement of the user may be identified based at least on the session and the at least one message. A diet suggestion for the user may be obtained based at least on the diet intention, the diet information and the diet requirement. A response including the diet suggestion may be generated and provided to the user.

19 Claims, 16 Drawing Sheets

(51) Int. Cl.
  *G06F 16/9032*  (2019.01)
  *G06F 16/9535*  (2019.01)
  *G06F 16/2457*  (2019.01)
  *G06N 5/02*  (2006.01)
  *G09B 7/02*  (2006.01)
  *H04L 51/02*  (2022.01)

(52) U.S. Cl.
  CPC ........... *G06F 16/9535* (2019.01); *G06N 5/02* (2013.01); *G09B 7/02* (2013.01); *G09B 19/003* (2013.01); *G16H 20/60* (2018.01); *H04L 51/02* (2013.01)

(56) References Cited

U.S. PATENT DOCUMENTS

| | | | | |
|---|---|---|---|---|
| 2013/0149679 | A1* | 6/2013 | Tokuda | A47J 36/321 |
| | | | | 434/127 |
| 2015/0294595 | A1* | 10/2015 | Hu | G06Q 10/101 |
| | | | | 434/127 |
| 2017/0228364 | A1* | 8/2017 | Byron | G06F 40/253 |
| 2017/0316488 | A1* | 11/2017 | Kremen | G09B 5/06 |
| 2017/0330481 | A1* | 11/2017 | Sabourian-Tarwe | ............... |
| | | | | G06Q 50/12 |
| 2018/0108272 | A1* | 4/2018 | Ahmad | G16H 50/70 |

FOREIGN PATENT DOCUMENTS

| | | |
|---|---|---|
| CN | 105426436 A | 3/2016 |
| CN | 107045587 A | 8/2017 |

\* cited by examiner

PROVIDING DIET ASSISTANCE IN A SESSION

CROSS-REFERENCE TO RELATED APPLICATION

This application is a U.S. National Stage Filing under 35 U.S.C. 371 of International Patent Application Serial No. PCT/CN2017/102141, filed Sep. 18, 2017, and published as WO 2019/051847 A1 on Mar. 21, 2019, which application and publication are incorporated herein by reference in their entirety.

BACKGROUND

Artificial Intelligence (AI) chatbot is becoming more and more popular, and is being applied in an increasing number of scenarios. The chatbot is designed to simulate people's conversation, and may chat with users by text, speech, image, etc. Generally, the chatbot may scan for keywords within a message input by a user or apply natural language processing on the message, and provide a response with the most matching keywords or the most similar wording pattern to the user.

SUMMARY

This Summary is provided to introduce a selection of concepts that are further described below in the Detailed Description. It is not intended to identify key features or essential features of the claimed subject matter, nor is it intended to be used to limit the scope of the claimed subject matter.

Embodiments of the present disclosure propose method and apparatus for providing diet assistance to a user in a session. At least one message may be received in the session, the session being between the user and an electronic conversational agent. A diet intention associated with the user may be deduced based on the session and the at least one message. Diet information may be extracted from the at least one message. A diet requirement of the user may be identified based at least on the session and the at least one message. A diet suggestion for the user may be obtained based at least on the diet intention, the diet information and the diet requirement. A response including the diet suggestion may be generated and provided to the user.

It should be noted that the above one or more aspects comprise the features hereinafter fully described and particularly pointed out in the claims. The following description and the drawings set forth in detail certain illustrative features of the one or more aspects. These features are only indicative of the various ways in which the principles of various aspects may be employed, and this disclosure is intended to include all such aspects and their equivalents.

BRIEF DESCRIPTION OF THE DRAWINGS

The disclosed aspects will hereinafter be described in connection with the appended drawings that are provided to illustrate and not to limit the disclosed aspects.

DETAILED DESCRIPTION

Figure 1:
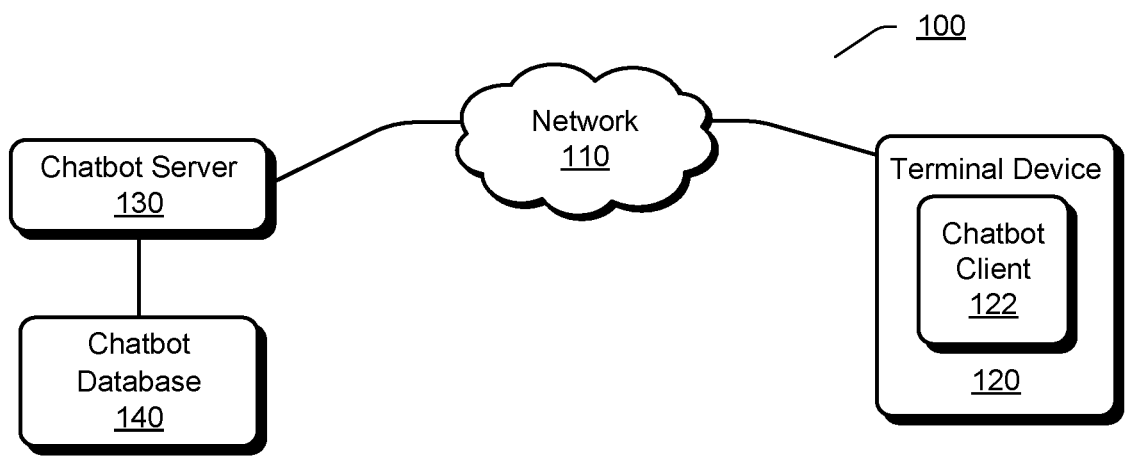
FIG. 1 illustrates an exemplary network architecture deploying a chatbot according to an embodiment.

The present disclosure will now be discussed with reference to several example implementations. It is to be understood that these implementations are discussed only for enabling those skilled in the art to better understand and thus implement the embodiments of the present disclosure, rather than suggesting any limitations on the scope of the present disclosure.

Various diet related questions or problems may exist in people's life. For example, people may want to know what kinds of food are beneficial for short-time recovering from some diseases or hurts, or beneficial for long-time physical health or prevention of some diseases. Usually, people may browse health or diet related websites by themselves to find answers, or search relevant information via search engines which can index content on the health or diet related websites and provide searching results that semantically match people's query. However, either proactive browsing or search engine based information retrieving are time-consuming, and the obtained information is more general-oriented without referring to personalized information of people. Moreover, for example, people may meet such problem that, when cooking, they don't know how to cook with some cooking ingredients. It is time-consuming to obtain recipes from diet or cooking related websites, and those recipes available on the network may be not related to the cooking ingredients that are interested by people.

Embodiments of the present disclosure propose to provide diet assistance to a user in a session between the user and an electronic conversational agent. The electronic conversational agent may be, such as, a chatbot. Conventionally, a chatbot may conduct automated sessions with a user. Herein, "session" may refer to a time-continuous dialog between two chatting participants and may include messages and responses in the dialog, wherein "message" refers to any information input by the user, e.g., queries from the user, answers of the user to questions from the chatbot, opinions of the user, etc., and "response" refers to any information provided by the chatbot, e.g., answers of the chatbot to questions from the user, comments of the chatbot, etc. The term "message" and the term "query" may also be interchangeably used.

The embodiments of the present disclosure may provide diet assistance based on the user's personalized information, such as, the user's health condition, concerned disease, cooking method preference, taste preference, etc. The diet assistance may include various diet suggestions. In some aspects, the diet assistance provided by the chatbot to the user may be diet knowledge that is related to the user's query about food, dish, concerned disease, etc. Herein, "food" may refer to things that may be eaten or drunk by people and obtained without cooking or with limited cooking procedures, and "dish" may refer to an edible item formed by prepared foods through cooking. However, the term "food" and the term "dish" may also be interchangeably used. In some aspects, the diet assistance provided by the chatbot to the user may be diet recommendation or product recommendation, such as, recommended foods or dishes, product information from partner entities, etc. In some aspects, the diet assistance provided by the chatbot to the user may be recipe recommendation, such as, existing recipes or newly-generated recipes. In some aspects, the diet assistance provided by the chatbot to the user may be cooking guidance, such as, a guidance of how to cook according to a recipe.

FIG. 1 illustrates an exemplary network architecture 100 deploying a chatbot according to an embodiment.

In FIG. 1, a network 110 is applied for interconnecting among a terminal device 120 and a chatbot server 130.

The network 110 may be any type of networks capable of interconnecting network entities. The network 110 may be a single network or a combination of various networks. In terms of coverage range, the network 110 may be a Local Area Network (LAN), a Wide Area Network (WAN), etc. In terms of carrying medium, the network 110 may be a wireline network, a wireless network, etc. In terms of data switching techniques, the network 110 may be a circuit switching network, a packet switching network, etc.

The terminal device 120 may be any type of electronic computing devices capable of connecting to the network 110, assessing servers or websites on the network 110, processing data or signals, etc. For example, the terminal device 120 may be desktop computers, laptops, tablets, smart phones, AI terminals, etc. Although only one terminal device is shown in FIG. 1, it should be appreciated that a different number of terminal devices may connect to the network 110.

In an implementation, the terminal device 120 may be used by a user. The terminal device 120 may include a chatbot client 122 which may provide automated chatting service for the user. In some cases, the chatbot client 122 may interact with the chatbot server 130. For example, the chatbot client 122 may transmit messages input by the user to the chatbot server 130, and receive responses associated with the messages from the chatbot server 130. However, it should be appreciated that, in other cases, instead of interacting with the chatbot server 130, the chatbot client 122 may also locally generate responses to messages input by the user.

The chatbot server 130 may connect to or incorporate a chatbot database 140. The chatbot database 140 may comprise information that can be used by the chatbot server 130 for generating responses.

It should be appreciated that all the network entities shown in FIG. 1 are exemplary, and depending on specific application requirements, any other network entities may be involved in the application scenario 100.

Figure 2:
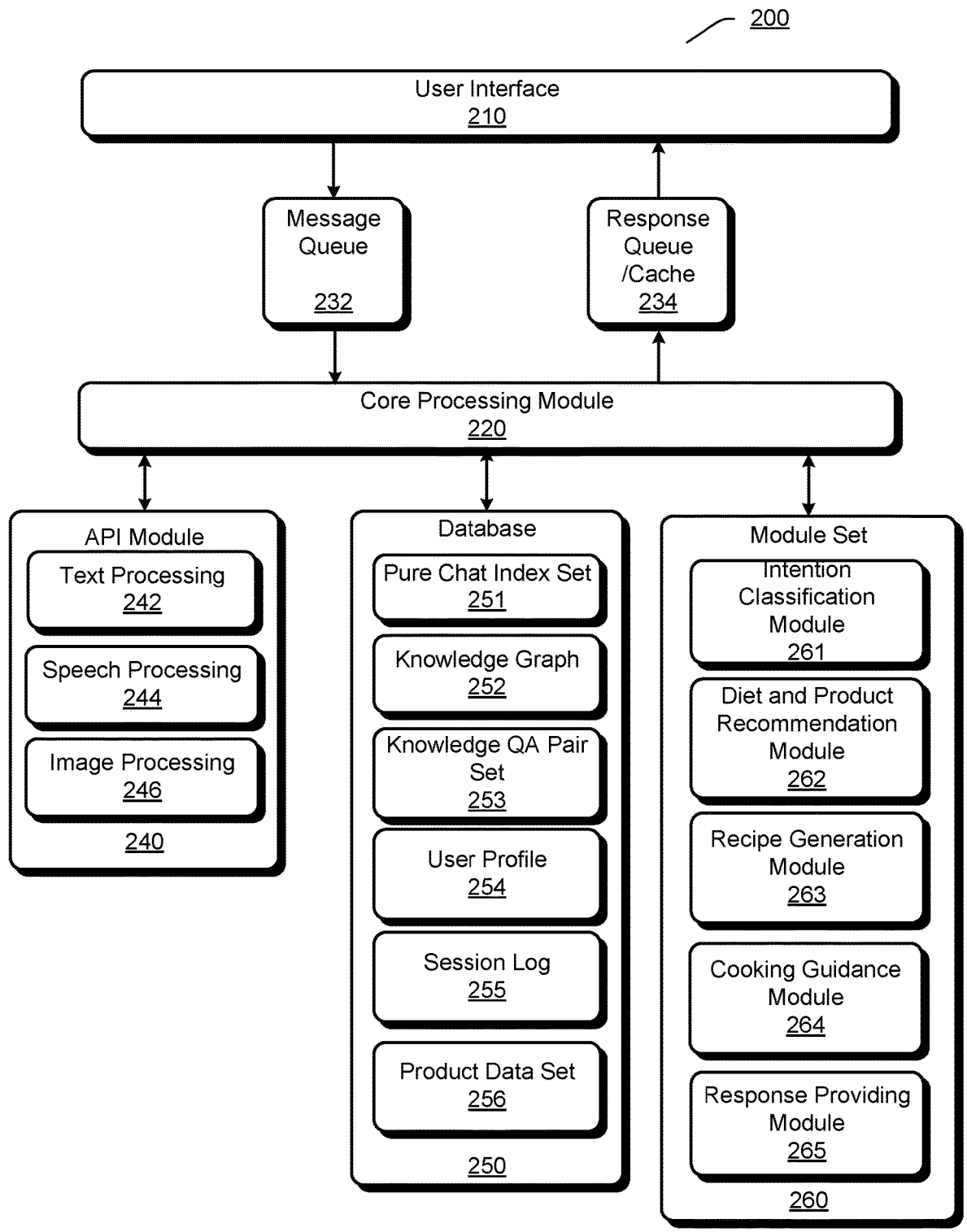
FIG. 2 illustrates an exemplary chatbot system according to an embodiment.

FIG. 2 illustrates an exemplary chatbot system 200 according to an embodiment.

The chatbot system 200 may comprise a user interface (UI) 210 for presenting a chat window. The chat window may be used by the chatbot for interacting with a user.

The chatbot system 200 may comprise a core processing module 220. The core processing module 220 is configured for, during operation of the chatbot, providing processing capabilities through cooperation with other modules of the chatbot system 200.

The core processing module 220 may obtain messages input by the user in the chat window, and store the messages in the message queue 232. The messages may be in various multimedia forms, such as, text, speech, image, video, etc.

The core processing module 220 may process the messages in the message queue 232 in a first-in-first-out manner. The core processing module 220 may invoke processing units in an application program interface (API) module 240 for processing various forms of messages. The API module 240 may comprise a text processing unit 242, a speech processing unit 244, an image processing unit 246, etc.

For a text message, the text processing unit 242 may perform text understanding on the text message, and the core processing module 220 may further determine a text response.

For a speech message, the speech processing unit 244 may perform a speech-to-text conversion on the speech message to obtain text sentences, the text processing unit 242 may perform text understanding on the obtained text sentences, and the core processing module 220 may further determine a text response. If it is determined to provide a response in speech, the speech processing unit 244 may perform a text-to-speech conversion on the text response to generate a corresponding speech response.

For an image message, the image processing unit 246 may perform image recognition on the image message to generate corresponding texts, and the core processing module 220 may further determine a text response. In some cases, the image processing unit 246 may also be used for obtaining an image response based on the text response.

Moreover, although not shown in FIG. 2, the API module 240 may also comprise any other processing units. For example, the API module 240 may comprise a video processing unit for cooperating with the core processing module 220 to process a video message and determine a response.

The core processing module 220 may determine responses through a database 250. The database 250 may comprise a plurality of index items that can be retrieved by the core processing module 220 for determining responses.

The database 250 may comprise a pure chat index set 251. The pure chat index set 251 may comprise index items that are prepared for free chatting between the chatbot and users, and may be established with data from, e.g., social networks.

The index items in the pure chat index set 251 may or may not be in a form of question-answer (QA) pair, e.g., <question, answer>. Question-answer pair may also be referred to as message-response pair.

The database 250 may comprise a knowledge graph 252. Herein, the knowledge graph 252 may refer to a single knowledge graph or a plurality of knowledge graphs in various domains. Knowledge information in the knowledge graph 252 may be in a form of tuple. The knowledge graph 252 may comprise a medical domain knowledge graph which includes knowledge information related to various diseases. The medical domain knowledge graph may further comprise sub-domain topics formed by various diseases respectively. The knowledge graph 252 may comprise a food domain knowledge graph which includes knowledge information related to various foods. The knowledge graph 252 may also comprise a knowledge graph that is related to both diseases and foods.

The database 250 may comprise a knowledge QA pair set 253. The knowledge QA pair set 253 may be formed by the knowledge graph 252, and may include knowledge information in a form of QA pair.

The database 250 may comprise a user profile 254. The user profile 254 may comprise personalized information of a user. For example, the user profile 254 may comprise the user's gender, age, location, health condition, cooking method preference, taste preference, etc.

The database 250 may comprise a session log 255. The session log 255 may comprise records of conversation contents in sessions between the chatbot and the user, such as, messages from the user, responses by the chatbot, etc.

The database 250 may comprise a product data set 256. The product data set 256 may comprise diet related product information of various partner entities. Herein, "product" may refer to commodities or services, the partner entities may be producers or sellers of commodities or providers of services from which the chatbot may obtain product information, and "product information" may include commodity information, service information, information of partner entity, etc.

The chatbot system 200 may comprise a module set 260 which is a collection of functional modules that can be operated by the core processing module 220 to generate or obtain responses.

The module set 260 may comprise an intention classification module 261. The intention classification module 261 may be configured for deducing or determining a diet intention of the user. Herein, "diet intention" may refer to diet related purposes or desires of the user that are explicitly or implicitly expressed in a session between the user and the chatbot. The intention classification module 261 may deduce various diet intentions based on at least one of the user's session log, current or latest message, user profile, etc. The diet intention may comprise diet knowledge acquisition which indicates that the user may want to get diet related knowledge. The diet intention may comprise diet recommendation which indicates that the user may want to get some recommendations of diet that are related to the user's diet concerns. The diet intention may comprise product recommendation which indicates that the user may be willing to receive diet related product information. The diet intention may comprise recipe recommendation which indicates that the user needs to have a recipe that is based at least on cooking ingredients of interest. In some cases, the diet intention may also be "no intention" which indicates that the user has no specific diet related intention in the session or no diet related intention can be deduced.

The module set 260 may comprise a diet and product recommendation module 262. The diet and product recommendation module 262 may be configured for generating or determining diet recommendation or product recommendation to the user based on at least one of the knowledge graph 252, the knowledge QA pair set 253, the user profile 254, the product data set 256, etc.

The module set 260 may comprise a recipe generation module 263. The recipe generation module 263 may be configured for generating a recipe based on cooking ingredients of interest, the user's cooking method or taste preference, etc. The recipe may be a newly-generated recipe which meets the user's need.

The module set 260 may comprise a cooking guidance module 264. The cooking guidance module 264 may be configured for guiding the user to cook following a recipe. For example, the guidance may be conducted via speech, text, image, video, etc.

The module set 260 may comprise a response providing module 265. The response providing module 265 may be configured for providing or transferring a response to a message of the user. In some implementations, the response may be generated or determined by the response providing module 265. For example, when no intention is deduced by the intention classification module 261, the response providing module 265 may determine a response from, such as, the pure chat index set 251. For example, when the diet intention is deduced as diet knowledge acquirement, the response providing module 265 may determine a response from, such as, the knowledge graph 252, the knowledge QA pair set 253, etc. In some implementations, the response provided by the response providing module 265 may be based on information from other modules. For example, the response providing module 265 may generate the response based on food/dish name or product information from the diet and product recommendation module 262, recipe from the recipe generation module 263, cooking guidance from the cooking guidance module 264, etc.

The core processing module 220 may provide determined responses to a response queue or response cache 234. For example, the response cache 234 may ensure that a sequence of responses can be displayed in a pre-defined time stream. Assuming that, for a message, there are no less than two responses determined by the core processing module 220, then a time-delay setting for the responses may be necessary. For example, if a message input by the user is "Did you eat your breakfast?", two responses may be determined, such as, a first response "Yes, I ate bread" and a second response "How about you? Still feeling hungry?". In this case, through the response cache 234, the chatbot may ensure that the first response is provided to the user immediately. Further, the chatbot may ensure that the second response is provided in a time delay, such as 1 or 2 seconds, so that the second response will be provided to the user 1 or 2 seconds after the first response. As such, the response cache 234 may manage the to-be-sent responses and appropriate timing for each response.

The responses in the response queue or response cache 234 may be further transferred to the UI 210 such that the responses can be displayed to the user in the chat window.

It should be appreciated that all the elements shown in the chatbot system 200 in FIG. 2 are exemplary, and depending on specific application requirements, any shown elements may be omitted and any other elements may be involved in the chatbot system 200.

Figure 3:
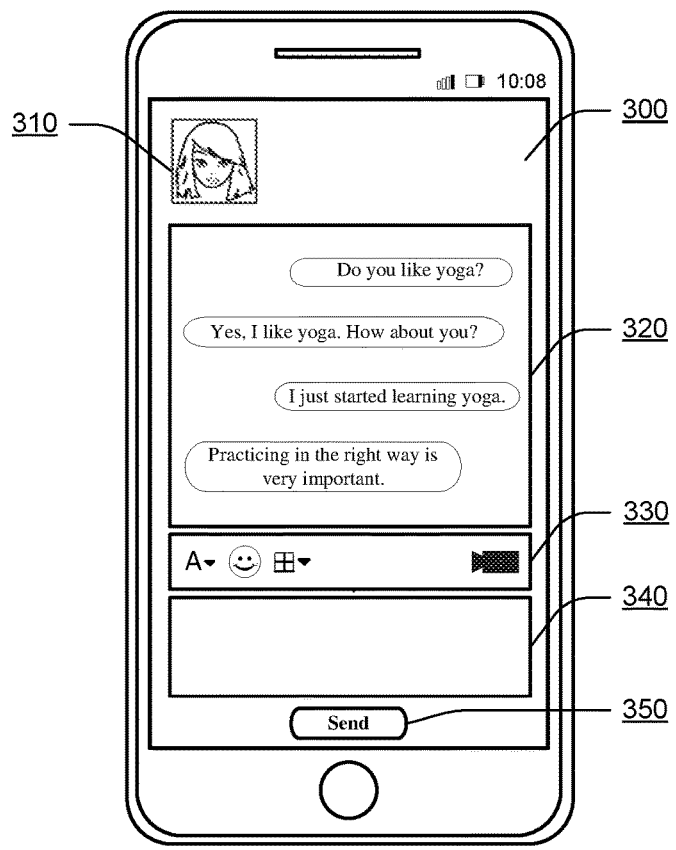
FIG. 3 illustrates an exemplary user interface according to an embodiment.

FIG. 3 illustrates an exemplary user interface 300 according to an embodiment.

The user interface 300 is included in a terminal device, and may comprise a chatbot icon 310, a presentation area 320, a control area 330 and an input area 340. The chatbot icon 310 may be a photo or picture representing the chatbot. The presentation area 320 displays a chat window that contains messages and responses in a session between a user and the chatbot. The control area 330 includes a plurality of virtual buttons for the user to perform message input settings. For example, the user may select to make a voice input, attach image files, select emoji symbols, make a short-cut of the current screen, activate camera, etc. through the control area 330. The input area 340 is used by the user for inputting messages. For example, the user may type text through the input area 340. The user interface 300 may further comprise a virtual button 350 for confirming to send input messages. If the user touches the virtual button 350, the messages input in the input area 340 may be sent to the presentation area 320.

It should be appreciated that all the elements and their layout shown in FIG. 3 are exemplary. Depending on specific application requirements, the user interface in FIG. 3 may omit or add any elements, and the layout of the elements in the user interface in FIG. 3 may also be changed in various approaches. For example, although the messages and responses are shown in a form of text in the presentation area 320, the messages and responses may also be in a form of speech. Accordingly, the chatbot and the user may chat by voices.

Figure 4:
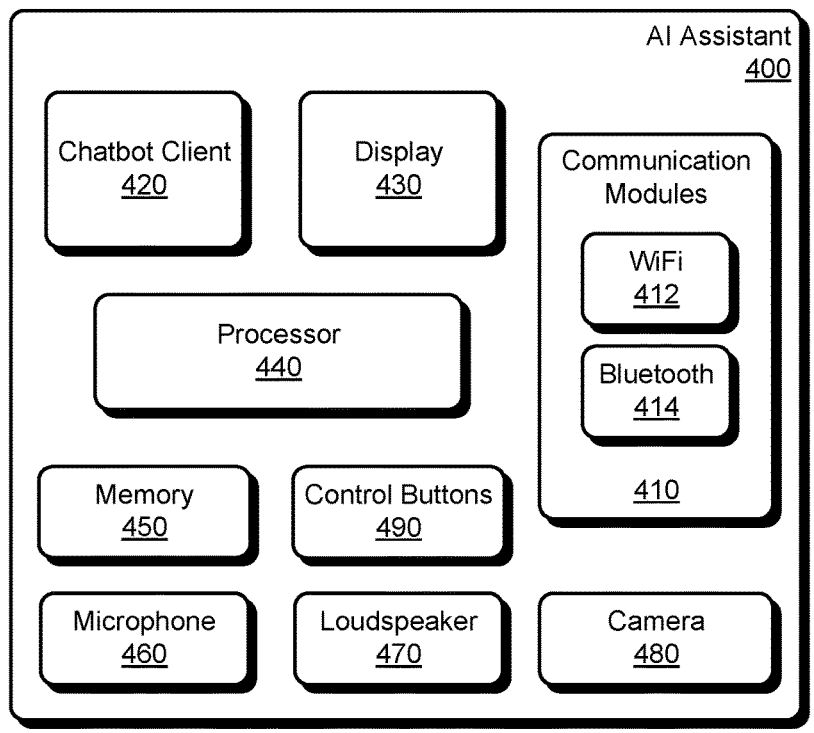
FIG. 4 illustrates exemplary hardware structure of an AI assistant according to an embodiment.

FIG. 4 illustrates exemplary hardware structure of an AI assistant 400 according to an embodiment. The AI assistant 400 may be various types of terminal device that operates the chatbot according to the embodiments of the present disclosure. In an implementation, the AI assistant 400 may be implemented as a portable device, such as, smart phone, intelligent wear product, etc., and may be carried by a user. In an implementation, the AI assistant 400 may be implemented as a separate and immovable hardware device, and placed at a designated place, such as, kitchen, bedroom, etc. In an implementation, the AI assistant 400 may be integrated into other devices, such as, a computer. In an implementation, the AI assistant 400 may be implemented in several separate devices, each of the devices performing a part of functions of the AI assistant 400.

As shown in FIG. 4, the AI assistant 400 may comprise communication modules 410. The communication modules 410 may enable the AI assistant 400 to access the network and communicate with other devices based on various communication techniques. For example, the communication modules 410 may comprise a WiFi module 412 for communicating based on the WiFi technique. The communication modules 410 may comprise a Bluetooth module 414 for communicating based on the Bluetooth technique. Although not shown, the communication modules 410 may further comprise any other modules for communicating based on any other communication techniques.

The AI assistant 400 may comprise a chatbot client 420. The chatbot client 420 may implement a part or all of functions of a chatbot. Thus, the AI assistant 400 may interact with a user, or a chatbot server through the chatbot client 420.

The AI assistant 400 may comprise a display 430. The display 430 may be used by the AI assistant 400 for, such as, presenting a user interface to a user.

The AI assistant 400 may comprise at least one processor 440 and a memory 450. The processor 440 may access data in the memory 450, execute computer-executable instructions stored in the memory 450, etc. For example, when executing the computer-executable instructions, the processor 440 may implement functions of the chatbot client 420. In some implementations, the processor 440 may be configured for performing various processes involved in methods for providing diet assistance according to the embodiments of the present disclosure.

The AI assistant 400 may comprise a microphone 460 and a loudspeaker 470. The microphone 460 and the loudspeaker 470 may be used for interacting with users through voices. Moreover, the AI assistant 400 may comprise at least one camera 480. The camera 480 may be used for capturing video or image, and thus the chatbot may detect, such as, the user's actions or expressions, as well as any other articles shot by the camera 480.

The AI assistant 400 may comprise one or more control buttons 490. The control buttons 490 may be physical or virtual buttons for controlling modules or functions in the AI assistant 400. For example, the control buttons 490 may comprise a volume control button for turning up or turning down voices.

It should be appreciated that all the modules shown in the AI assistant 400 are exemplary, and according to actual requirements, any of the modules may be omitted or replaced from the AI assistant 400, and any other modules may be added into the AI assistant 400. For example, in the case that the AI assistant 400 is designed for interacting with the user via voice only, even the display 430 may be omitted from the AI assistant 400.

Figure 5:
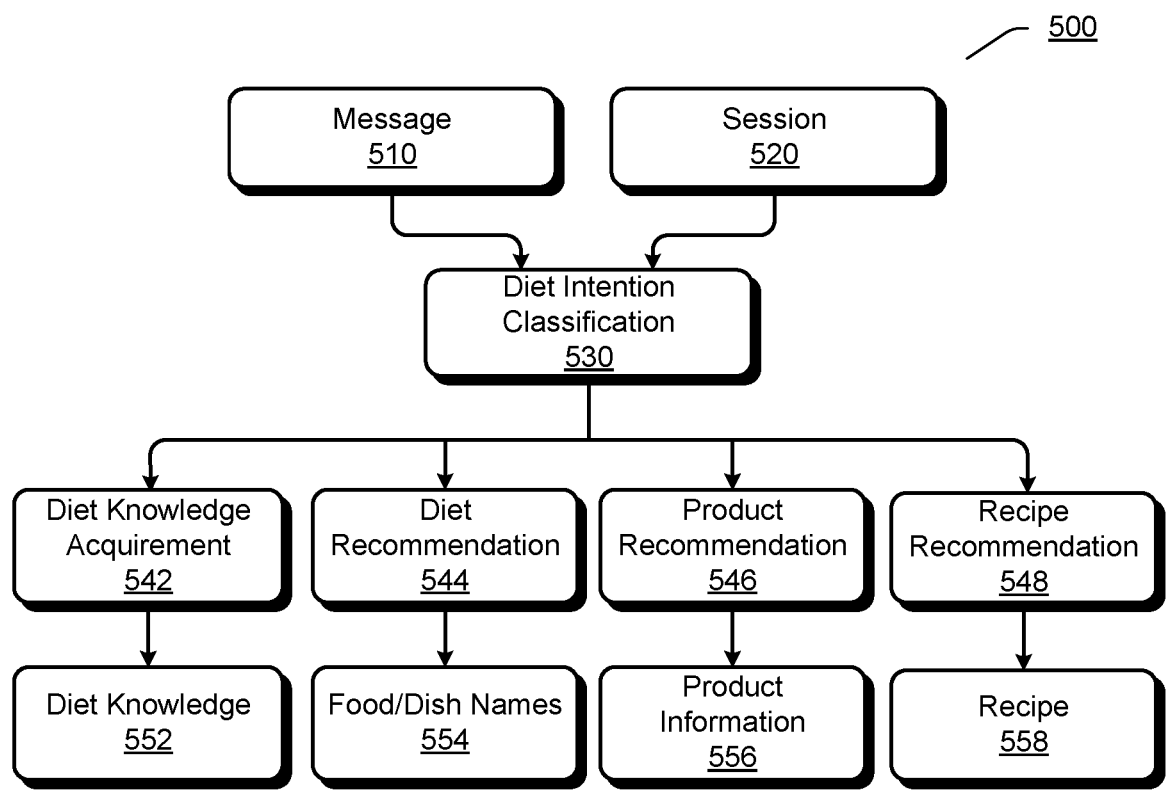
FIG. 5 illustrates an exemplary overall process for providing diet assistance according to an embodiment.

FIG. 5 illustrates an exemplary overall process 500 for providing diet assistance according to an embodiment. Through the process 500, a diet intention of a user may be determined, and a corresponding diet assistance procedure may be invoked to obtain a diet suggestion.

Message 510 and session 520 may be taken as inputs to diet intention classification 530. Herein, the message 510 may refer to one or more current or latest messages of the user, and the session 520 may refer to a record of the conversation between the user and the chatbot, such as, a session log of the user. The message 510 may be in a form of text, speech or image. Since a speech or image message may be converted to a corresponding text message, the following discussion will take text message as an example.

Moreover, although not shown, a user profile of the user may also be taken as an input to the diet intention classification 530.

The process of the diet intention classification 530 may be performed for deducing a diet intention of the user. When the diet intention is obtained, the chatbot may further determine a diet suggestion to the user accordingly.

In an implementation, the diet intention may be diet knowledge acquirement 542. For example, during the session, if the user is consulting how a diabetic patient should eat, the diet intention of the user may be deduced as acquiring diet knowledge of foods suitable for a diabetic patient. Accordingly, the chatbot may retrieve diet knowledge 552 involving food type or food list that is related to diabetes mellitus, as a diet suggestion to the user.

In an implementation, the diet intention may be diet recommendation 544. For example, during the session, if the user is talking about some foods or dishes that he has eaten or are about to eat, or is requiring an advice for something to eat, the diet intention of the user may be deduced as requiring diet recommendation. Accordingly, the chatbot may determine food/dish names 554 as a diet suggestion to the user. The food/dish names 554 may be determined at least in consideration of the user's personalized information, such as, health condition, taste preference, etc. as indicated in the user profile. For example, if the user is a diabetic patient, the food/dish name 554 may be "Caesar Salad", which is suitable for a diabetic patient.

In an implementation, the diet intention may be product recommendation 546. For example, during the session, if the user is interested in or is asking information of low-sugar drinks, the diet intention of the user may be deduced as requiring recommendation of low-sugar products. Accordingly, the chatbot may determine product information 556 as a diet suggestion to the user. The product information 556 may be one or more low-sugar drink's names, such as, "Coke Zero", "Diet Coke", etc.

In an implementation, the diet intention may be recipe recommendation 548. For example, during the session, if the user indicates that he wants to cook a dish with banana and sweet potato, the diet intention of the user may be deduced as requiring recommendation of a recipe with banana and sweet potato as cooking ingredients. Accordingly, the chatbot may retrieve or generate a recipe 558 as a diet suggestion to the user, wherein the recipe 558 is based on banana and sweet potato and preferably based on the user's preference.

In an implementation, although not shown in FIG. 5, the diet intention classification 530 may determine "no intention" for the user, which indicates that the user has not a definite diet related intention yet. In this case, the chatbot may provide a response to the user in a free chatting way.

A support vector machine (SVM) model may be used for implementing the diet intention classification 530. Output of the SVM model may include a set of diet intentions, such as, diet knowledge acquisition, diet recommendation, product recommendation, recipe recommendation, etc. It should be appreciated that the above diet intentions are exemplary, and according to actual requirements, more or less diet intentions may be determined by the SVM model.

In an implementation, the following features may be used in the SVM model for training a nonlinear relationship between <query, session log, user profile> and a set of diet intentions, where "query" denotes a current message of the user.

User profile, including information about, such as, gender, age, location, health condition, cooking method preference, taste preference, etc.

Word ngrams: unigrams and bigrams for words in the query. For example, the query may include "Please generate a recipe . . . ", "Give me a suggestion of food for dieting", "What should I eat for diabetes mellitus?", "What should I eat for making me stronger?", etc.

Character ngrams: for each word in the query, character ngrams are extracted. For example, 4-grams and 5-grams are used in this model. The character ngrams is advantageous for Asian languages, such as, Chinese, Japanese, etc.

Word skip-grams: for all the trigrams and 4-grams in the query, one of the words is replaced by a symbol, such as, "*", to indicate the presence of non-contiguous words.

Brown cluster ngrams: Brown clusters are used for representing words in the query, and then unigrams and bigrams are extracted as features.

Part-of-speech (POS) tags: the presence or absence of POS tags is used as binary features.

Social network related words: number of hashtags, emoticons, elongated words, and punctuations in the query are used as features.

Word2vec cluster ngrams: the word2vec tool (Mikolov et al., 2013) may be used for learning 100-dimensional word embedding from a social network dataset. Then, K-means algorithm and cosine distance of word vectors may be employed to cluster the million-level vocabulary into, such as, 200 classes. The classes are used for representing generalized words in the query.

Words and their numbers in the query that are also included in a disease lexicon.

Words and their numbers in the query that are also included in a food lexicon.

It should be appreciated that the above discussed features for the SVM model are illustrative rather than limitative, and according to actual requirements, more or less features may be used by the SVM model.

Figure 6A:
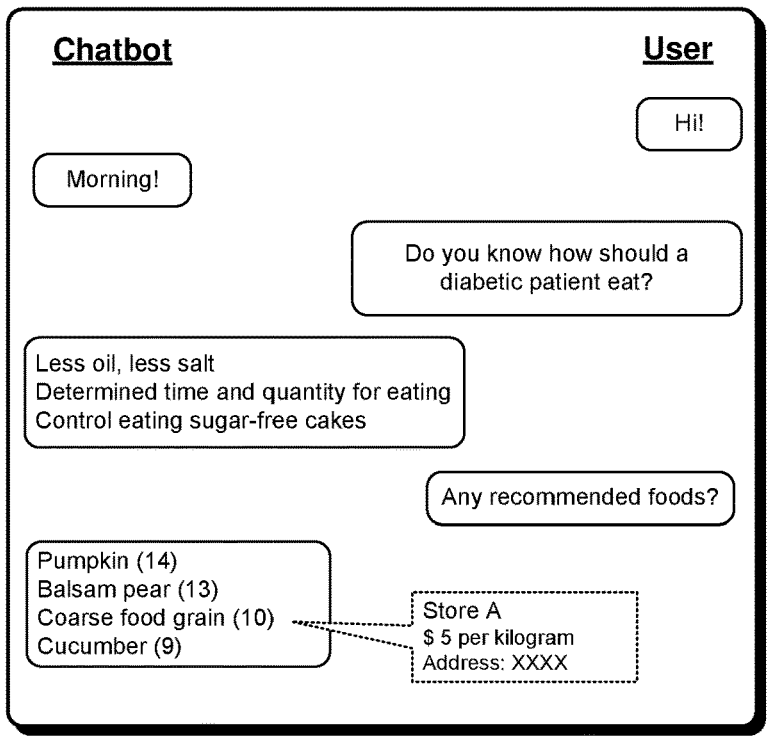
FIG. 6A and FIG. 6B illustrate exemplary chat windows according to an embodiment.

FIG. 6A illustrates an exemplary chat window 610 according to an embodiment. The chat window 610 shows an exemplary procedure for providing diet suggestions including diet knowledge, food/dish names and product information in a session according to the embodiment.

When receiving a message "Hi!" from the user in a session, the chatbot may give a response "Morning!" based on a pure chat index set.

When receiving a message "Do you know how should a diabetic patient eat?" in the session, the chatbot may determine, based at least on the session and the message, that the diet intention of the user is requiring diet knowledge of diabetes mellitus. The chatbot may extract diet information, such as, concerned disease "diabetes mellitus", from the message. Meanwhile, the chatbot may already know, from the user profile, a diet requirement of the user that health condition of the user is associated with diabetes mellitus. Then, based at least on the diet intention, the diet information and the diet requirement, the chatbot may obtain diet knowledge as a diet suggestion, such as, "Less oil, less salt", "Determined time and quantity for eating", "Control eating sugar-free cakes", etc. The chatbot may provide a corresponding response including the diet suggestion to the user.

When the user further inputs a message "Any recommended foods?", the chatbot may determine, based at least on the session and the message, that the diet intention of the user is acquiring diet and/or product recommendation for a diabetic patient. The chatbot may extract diet information, such as, concerned disease "diabetes mellitus" and food type "recommended foods for a diabetic patient", from the message and the previous message. Meanwhile, the diet requirement of the user indicates that the health condition of the user is associated with diabetes mellitus. Then, based at least on the diet intention, the diet information and the diet requirement, the chatbot may obtain food names or product information as a diet suggestion, such as, "Pumpkin (14)", "Balsam pear (13)", "Coarse food grain (10)", "Cucumber (9)", etc., wherein the numbers following food names indicate frequencies of the corresponding foods being given positive feedbacks by all the users. The chatbot may provide a corresponding response including the diet suggestion to the user. The response may also include links to product selling information. For example, if the user clicks on or moves the cursor onto "Coarse food grain (10)", corresponding selling information may be displayed, such as, "Store A", "$5 per kilogram", "Address: xxxx", etc.

Figure 6B:
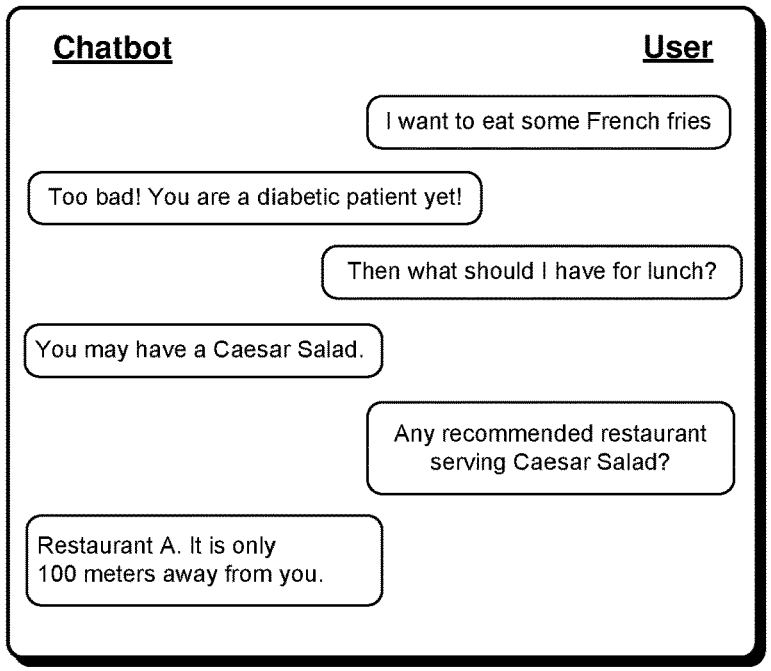

FIG. 6B illustrates an exemplary chat window 620 according to an embodiment. The chat window 620 shows an exemplary procedure for providing diet suggestions including food/dish names and product information in a session according to the embodiment.

When receiving a message "I want to eat some French Fries" from the user in the session, the chatbot may determine, based at least on the session and the message, that the diet intention of the user is requiring diet recommendation. The chatbot may extract diet information, such as, food name "French fries", from the message. Meanwhile, the chatbot may already know, from the user profile, a diet requirement of the user that health condition of the user is associated with diabetes mellitus. The chatbot may determine, based on such as a knowledge graph, that "French fries" is not a suitable food for a diabetic patient. Thus, based at least on the diet intention, the diet information and the diet requirement, the chatbot may obtain a diet suggestion about not recommending the user to eat French fries. For example, the chatbot may provide a corresponding response including the diet suggestion to the user, such as, "Too bad! You are a diabetic patient yet!".

When receiving a message "Then what should I have for lunch?" from the user, the chatbot may determine, based at least on the session and the message, that the diet intention of the user is acquiring diet recommendation. The chatbot may extract diet information, such as, food type "lunch", from the message. Meanwhile, the diet requirement of the user indicates that the health condition of the user is associated with diabetes mellitus. Then, based at least on the diet intention, the diet information and the diet requirement, the chatbot may obtain a dish name as a diet suggestion, such as, "Caesar Salad", wherein "Caesar Salad" is a suitable dish for a diabetic patient. Then the chatbot may provide a corresponding response including the diet suggestion to the user, such as, "You may have a Caesar Salad".

When the user further inputs a message "Any recommended restaurant serving Caesar Salad?", the chatbot may determine, based at least on the session and the message, that the diet intention of the user is acquiring product recommendation about Caesar Salad. The chatbot may extract diet information, such as, dish name "Caesar Salad", from the message. Meanwhile, the diet requirement of the user indicates that the health condition of the user is associated with diabetes mellitus. Then, based at least on the diet intention, the diet information and the diet requirement as well as the user's location as indicated in the user profile, the chatbot may obtain product information as a diet suggestion, such as, "Restaurant A", "100 meters away", etc. The chatbot may provide a corresponding response including the diet suggestion to the user, such as, "Restaurant A. It is only 100 meters away from you".

Figure 7:
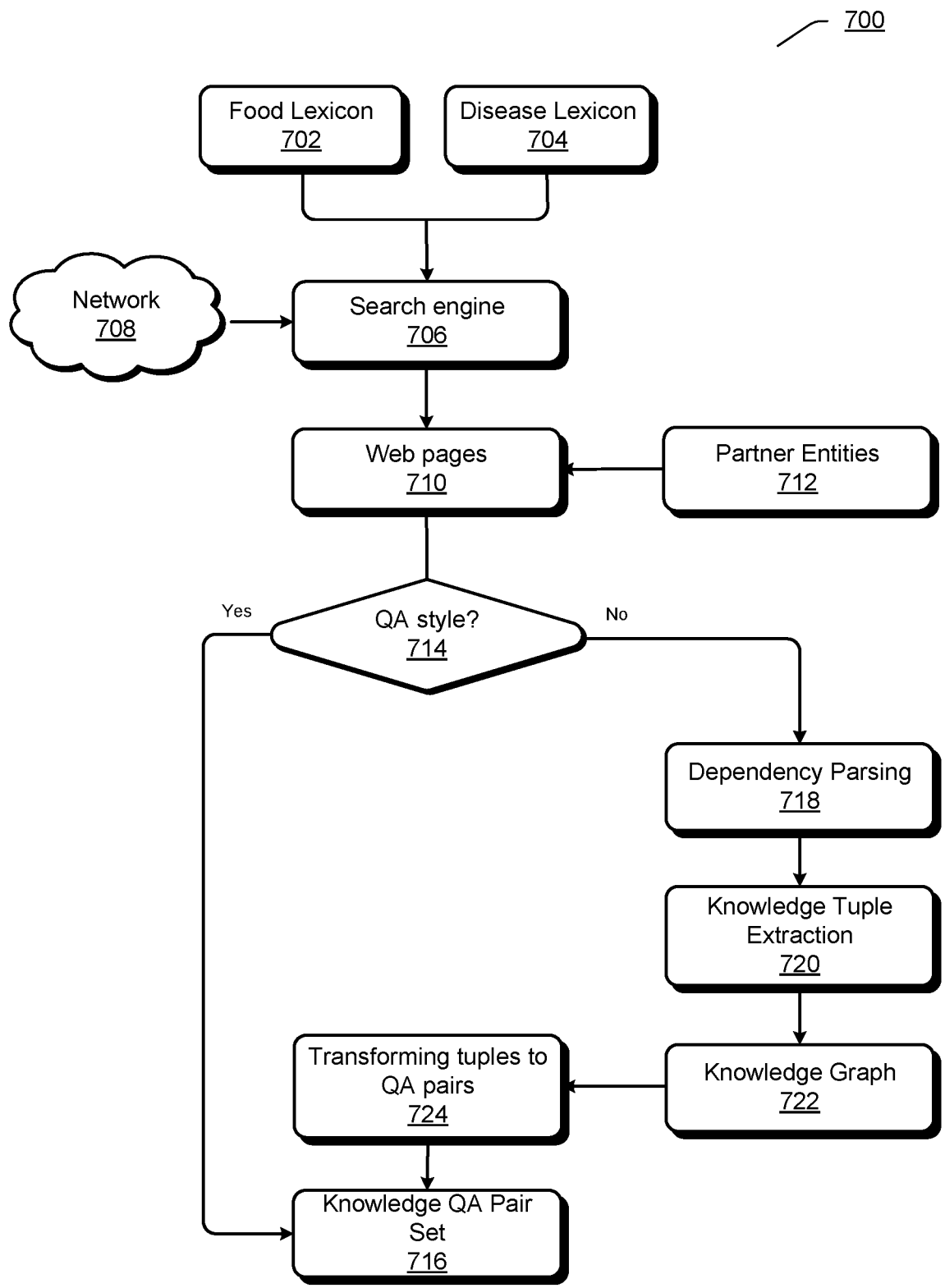
FIG. 7 illustrates an exemplary process for establishing knowledge graph and knowledge question-answer (QA) pair set according to an embodiment.

FIG. 7 illustrates an exemplary process 700 for establishing knowledge graph and knowledge QA pair set according to an embodiment.

At least one of a food lexicon 702 and a disease lexicon 704 may be used for providing searching keywords for a search engine 706. The food lexicon 702 comprises names of various foods or dishes, and the following discussions take "foods" as an example. The disease lexicon 704 comprises names of various diseases. It should be appreciated that any other types of lexicon may be used for providing searching keywords.

Each entry in the food lexicon 702 and the disease lexicon 704 may be provided to the search engine 706. The search engine 706 may crawl relevant web pages 710 from the network 708 by using the entry as a searching keyword. Additionally or alternatively, the web pages 710 may also be provided by partner entities 712. The partner entities 712 may be, such as, producers, sellers, restaurants, etc. that can supply the web pages 710 or related data. The web pages 710 may contain at least one type of food, at least one type of disease, or both, and thus the web pages 710 may be construed as including knowledge about foods and/or diseases.

At 714, it may be determined whether a web page is in a QA pair style, such as, in a form of <question, answer>. If yes, QA pairs in the web page may be added into a knowledge QA pair set 716. If not, that is, the web page is in a form of plain text, dependency parsing may be performed on the plain text at 718. Syntactic structures of sentences in the plain text may be identified through dependency parsing at 718, and then knowledge tuples may be extracted from dependency trees of the sentences at 720. The knowledge tuples may further form a knowledge graph 722.

Figure 8A:
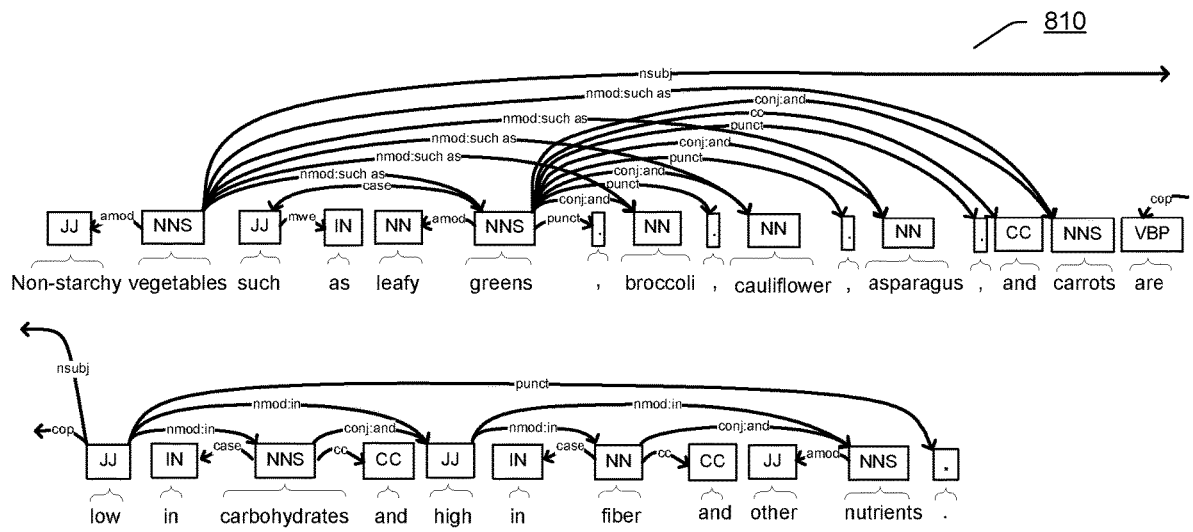
FIG. 8A and FIG. 8B illustrate exemplary dependency parsing according to an embodiment.
Figure 8B:
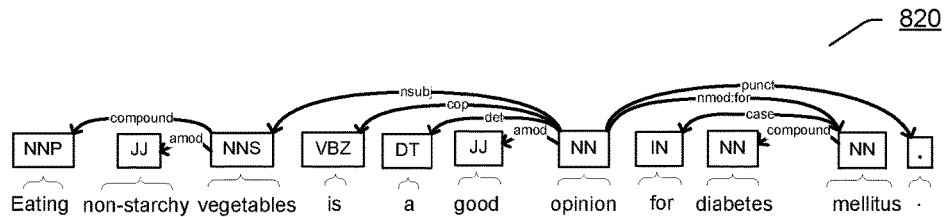

FIG. 8A and FIG. 8B illustrate exemplary dependency parsing according to an embodiment. FIG. 8A illustrates an exemplary dependency parsing 810 on a sentence "Non-starchy vegetables such as leafy greens, broccoli, cauliflower, asparagus, and carrots are low in carbohydrates and high in fiber and other nutrients.", and FIG. 8B illustrates an exemplary dependency parsing 820 on a sentence "Eating non-starchy vegetables is a good opinion for diabetes mellitus.". Dependency trees are obtained through performing the dependency parsing 810 and 820 on the sentences. It should be appreciated that various dependency parsing techniques may be used here for performing the dependency parsing.

Knowledge tuples may be extracted from the dependency trees of the sentences. The extracting process may follow dependency arcs which link predicates with arguments and link entities with syntactic relations.

It is assumed that the food lexicon 702 contains entities "non-starchy vegetables", "leafy greens", "broccoli", "cauliflower", "asparagus" and "carrots", and the disease lexicon 704 contains an entity "diabetes mellitus". Then, a food "non-starchy vegetables" and a disease "diabetes mellitus" may be linked by the following dependency arcs shown in FIG. 8A and FIG. 8B: <non-starchy vegetables, good opinion, nsubj> where "nsubj" denotes noun-style subject of the dependency arc; and <good opinion, diabetes mellitus, nmod:for> where "nmod:for" denotes a noun-style modification relation guided by keyword "for" between "good opinion" and "diabetes mellitus". Then, the following tuple may be obtained by combining these two dependency arcs together: <non-starchy vegetables, diabetes mellitus, good opinion>.

The above is an exemplary tuple in a form of <entity, entity, relation>, such as, <food, disease, relation>. Through this way, various available relationships for foods and diseases that appear in the plain text may be collected.

Moreover, relations of entities that are both foods or both diseases may also be extracted. Taking food entities as an example, the following dependency arcs are shown in FIG. 8A: <non-starchy vegetables, leafy greens, nmod:such_as> where "nmod" denotes a noun-style modification relation guided by key phrase "such as"; and <leafy greens, broccoli, conj :and> where "conj" is for conjunction and guided by keyword "and". If the "nmod:such_as" dependency type is mapped into "is_a" relation which is more generalized, then the following tuples of "is_a" relation may be obtained: <leafy greens, non-starchy vegetables, is a> which implies that "leafy greens is a non-starchy vegetable"; and <broccoli, non-starchy vegetables, is a> which implies that "broccoli is a non-starchy vegetable". Through this way, available relationships for foods that appear in the plain text may be collected. Similarly, available relationships for diseases that appear in the plain text may also be collected.

The extracted tuples may be used for forming or updating the knowledge graph 722. The knowledge graph 722 may be a medical domain knowledge graph which includes knowledge information related to various diseases. The knowledge graph 722 may be a food domain knowledge graph which includes knowledge information related to various foods. The knowledge graph 722 may also be a knowledge graph that is related to both diseases and foods.

In an implementation, a knowledge graph that is related to both diseases and foods may be obtained through linking a food domain knowledge graph and a medical domain knowledge graph. The linking may be based on at least one of the following heuristic rules:

Link by the knowledge tuples mined using both of the two lexicons: for example, regarding the tuples <non-starchy vegetables, diabetes mellitus, good opinion> and <non-starchy vegetables, leafy greens, nmod:such_as>, these two tuples may be linked based on the same or similar words "non-starchy vegetables".

Link by co-occurrence frequencies of one disease and one food that appear in one sentence, one paragraph, or even one document. Different similarity scores may be assigned based on these co-occurrences so that diseases and foods can be linked making use of these similarity scores.

Link by latent semantic similarity scores. A joint word2vec model may be trained using disease domain and food domain web pages, and then may be used for computing "latent semantic scores" of a pair of <disease, food> by dot-product of their vector representations. For example, assuming there is a tuple <leafy greens, diabetes mellitus, good opinion>, and it is determined by the word2vec model that "leafy greens" and "broccoli" have high semantic similarity, thus an extended tuple <broccoli, diabetes mellitus, good opinion> may be obtained.

The tuples in the knowledge graph 722 may be transformed to QA pairs at 724. Taking a tuple <diabetes mellitus, pumpkin, suitable food> as an example, this tuple describes the relation "suitable food" between an entity "diabetes mellitus", which is a disease name, and an entity "pumpkin", which is a food name. This tuple may be transformed to the following question-answer pairs:

Question=What is the suitable food for diabetes mellitus? Answer=Pumpkin.
Question=Is pumpkin suitable food for diabetes mellitus? Answer=Yes, it is.
Question=What kind of disease is pumpkin a suitable food? Answer=Diabetes mellitus.

In this way, one tuple may be automatically transformed into a plurality of QA pairs in natural language. These natural language style QA pairs may be used for providing natural language style responses to the user. The QA pairs transformed from knowledge tuples may be added into the knowledge QA pair set 716.

A learning-to-rank (LTR) model may be used for ranking candidate answers in the knowledge QA pair set 716 by giving a query of the user. In some implementations, latent semantic features may be adopted for comparing a query and a candidate <question, answer> pair in a dense vector space.

In an implementation, "dependency arc matching" score may be adopted in the LTR model. Both the query and a question or answer in each candidate <question, answer> pair may be performed dependency parsing, and then dependency arcs of the query and the question or answer may be compared to obtain a similarity score.

Figure 9A:
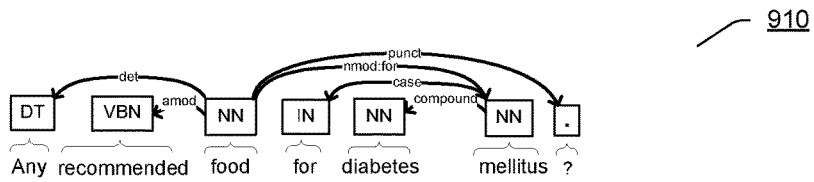
FIG. 9A and FIG. 9B illustrate exemplary dependency parsing according to an embodiment.
Figure 9B:
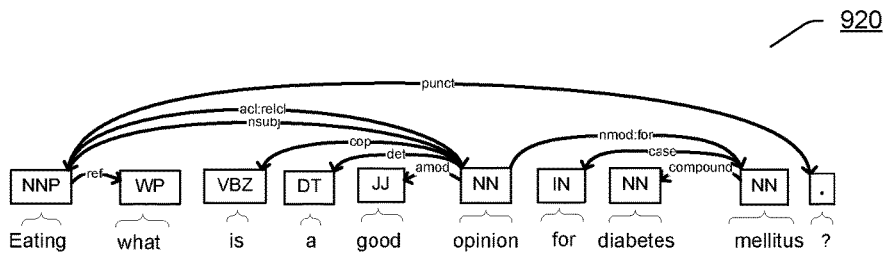

Given a query "Any recommended food for diabetes mellitus?", FIG. 9A illustrates an exemplary dependency parsing 910 on this query according to an embodiment. Moreover, given a question "Eating what is a good opinion for diabetes mellitus?" in a candidate <question, answer> pair, FIG. 9B illustrates an exemplary dependency parsing 920 on this question according to an embodiment.

The query and the question share the same dependency arcs, such as, "diabetes-compound-mellitus", "for-case-mellitus", etc., which are explicit word and arc matching. Moreover, similar dependency arcs are also shared between the query and the question, which are implicit dense vector space matching, such as, "food-nmod:for-mellitus" in the query is similar with "opinion-nmod:for-mellitus" in the question, "recommended-amod-food" in the query is similar with "good-amod-opinion" in the question, etc. The comparison of dependency arcs may be performed in latent vector spaces, through projecting the dependency arcs into dense space vectors and then computing similarity scores of the two vectors by, such as, cosine function.

In an implementation, the LTR model may employ a gradient boosting decision tree (GBDT) algorithm for ranking candidate QA pairs for a query, and the following features may be utilized in the GBDT algorithm.

Implicit/explicit dependency arc similarity score between the dependency trees of the query and the candidate question. The explicit dependency arc similarity score is obtained based on text string level comparison of the dependency arcs. The implicit dependency arc similarity score is obtained based on dense space vector level comparison of the dependency arcs.

Implicit/explicit dependency arc similarity score between the dependency trees of the query and the candidate answer.

Frequency of the user's and other users' positive feedbacks for the candidate answer.

Language model for information retrieval with respect to the query q and the candidate question Q: Given a query q and a candidate question Q, this feature measures the relevance between q and Q through:

$$P(q|Q) = \Pi_{w \in q}[(1-\lambda)P_{ml}(w|Q) + \lambda P_{ml}(w|C)] \quad \text{Equation (1)}$$

where $P_{ml}(w|Q)$ is the maximum likelihood of word w estimated from Q, and $P_{ml}(w|C)$ is a smoothing item that is computed as the maximum likelihood estimation in a large-scale corpus C. Here the corpus C may be the knowledge QA pair set. The smoothing item avoids zero probability, which stems from those words appearing in the candidate question Q but not in the query q. The is a parameter that acts as a trade-off between the likelihood and the smoothing item, where $\lambda \in (0, 1)$. This feature works well when there are a number of words overlapped between the query and the candidate question.

Language model for information retrieval with respect to the query q and the candidate answer A. In this language model, similarity score between the query and a candidate answer is also computed using Equation (1) by taking the candidate answer A instead of Q in Equation (1).

Translation-based language models with respect to the query q and the candidate question Q. This feature learns word-to-word and/or phrase-to-phrase translation probability from, such as, question-answer pairs, and incorporates the learned information into maximum likelihood.

Given the query q and the candidate question Q, translation-based language model is defined as:

$$P_{trb}(q|Q) = \Pi_{w \in q}[(1-\lambda)P_{mx}(W|Q) + \lambda P_{ml}(w|C)] \quad \text{Equation (2)}$$

$$P_{mx}(w|Q) = \alpha P_{ml}(w|Q) + \beta P_{tr}(w|Q) \quad \text{Equation (3)}$$

$$P_{tr}(w|Q) = \Sigma_{v \in Q} P_{tp}(w|v) P_{ml}(v \equiv Q) \quad \text{Equation (4)}$$

Here $\lambda$, $\alpha$ and $\beta$ are parameters satisfying $\lambda \in (0, 1)$ and $\alpha+\beta=1$. $P_{tp}(w|v)$ is a translation probability from word v in Q to word w in q.

Translation-based language models with respect to the query q and the candidate answer A. In this language model, similarity score between the query and the candidate answer is also computed using Equations (2)-(4) by taking the candidate answer A instead of the Q in Equations (2)-(4).

Edit distance between the query and the candidate question in a word or character level.

Maximum subsequence ratio between the query and the candidate question.

Recurrent neural network (RNN) by using gated recurrent units (GRUs) as encoding. The encoding projects a sequence of words, a sequence of phrases, or a sequence of dependency arcs into a dense vector space, which is a latent semantic representation of the sequence. The query and the candidate question or answer may be provided to a RNN-GRU layer respectively to obtain corresponding dense vectors, and then similar score between the two dense vectors may be computed.

It should be appreciated that all the above features in the GBDT algorithm are exemplary, and more or less features may be adopted in the GBDT algorithm in various implementations.

Figure 10:
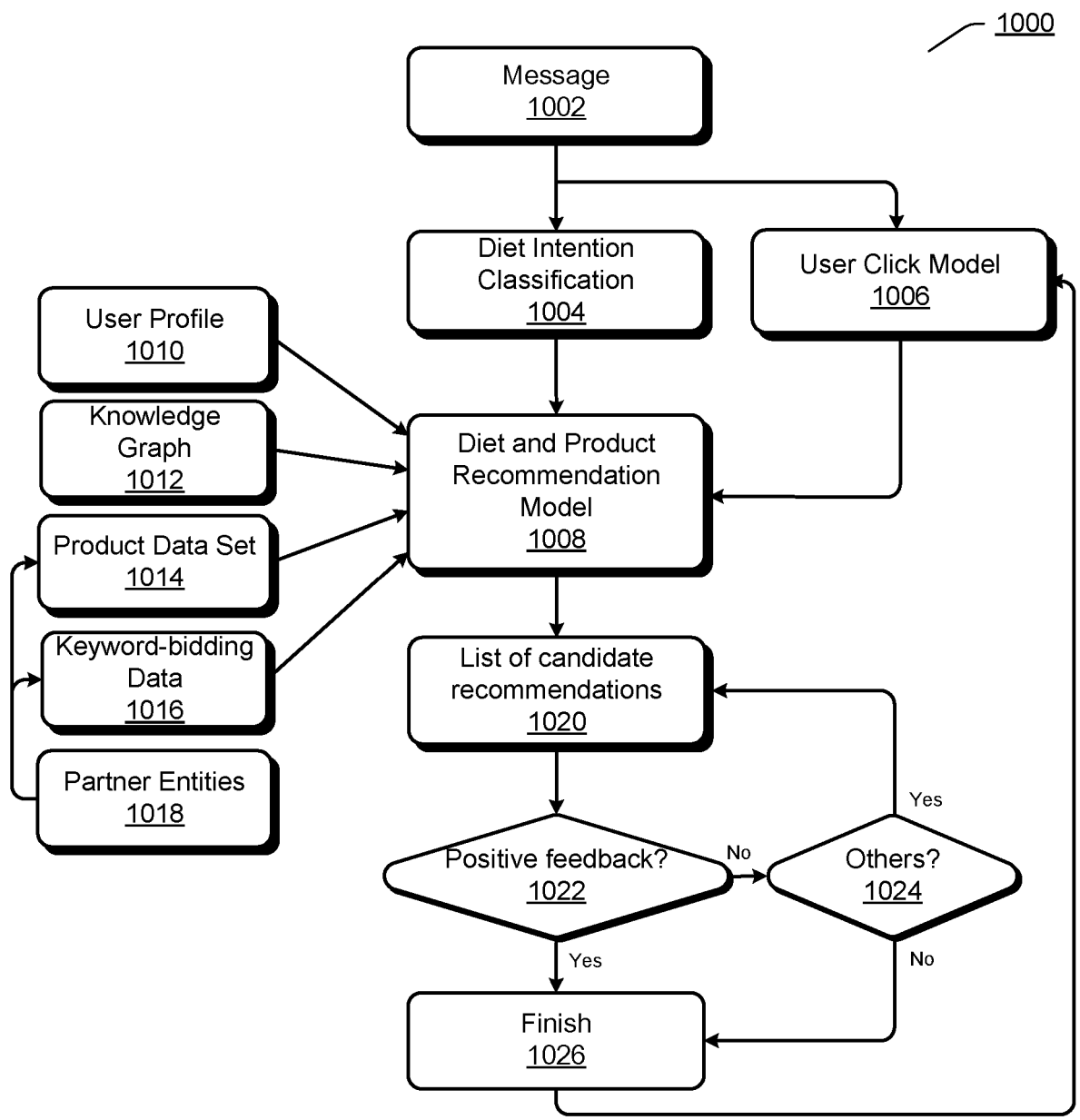
FIG. 10 illustrates an exemplary process for providing diet and product recommendation according to an embodiment.

FIG. 10 illustrates an exemplary process 1000 for providing diet and product recommendation according to an embodiment.

At 1002, at least one message may be received in a session.

At 1004, diet intention classification may be performed in a way as discussed above in connection with the operation at 530 in FIG. 5. In the scenario of FIG. 10, the diet intention of the user may be determined as diet recommendation or product recommendation.

At 1008, a diet and product recommendation model may be used for providing diet recommendation or product recommendation, such as, food/dish names, product information, etc. The diet and product recommendation model may rank a plurality of diet or product recommendations and provide a list of candidate recommendations 1020 to the user.

Besides the output of the diet intention classification is taken as an input to the diet and product recommendation model, the diet and product recommendation model may further take an output of a user click model 1006 as an input.

The user click model may predict click-through-rate (CTR) of candidate recommendations with respect to a query from the user. Inputs for the user click model may comprise, such as, user id, session log, historical click record, user profile, current query, etc., and output of the user click model is predications of CTRs of candidate recommendations.

As shown in FIG. 10, an arrow is connected from "Finish" block 1026 to the user click model 1006 so as to transfer a feedback, thus the user's click behaviors to candidate recommendations may be updated online. The user click model may store the user's historical click record and retrain itself during a given time interval, such as, per day, per week, etc.

In an implementation, a logistic regression model may be trained using the following features to implement the user click model. The logistic regression model is advantageous for it is easy to be trained or retrained and has a fast decoding speed.

User profile, including information about, such as, gender, age, location, health condition, cooking method preference, taste preference, etc.

User's historical click record: an exemplary format of the record is <user id, candidate recommendation, click count>.

Word ngrams: unigrams and bigrams for words in the query.

Character ngrams: for each word in the query, character ngrams are extracted. For example, 4-grams and 5-grams are used in this model.

Word skip-grams: for all the trigrams and 4-grams in the query, one of the words is replaced by a symbol, such as, "*", to indicate the presence of non-contiguous words.

Brown cluster ngrams: Brown clusters are used for representing words in query, and then unigrams and bigrams are extracted as features.

Part-of-speech (POS) tags: the presence or absence of POS tags is used as binary features.

Social network related words: number of hashtags, emoticons, elongated words, and punctuations in the query are used as features.

Word2vec cluster ngrams: the word2vec tool (Mikolov et al., 2013) may be used for learning 100-dimensional word embedding from a social network dataset. Then, K-means algorithm and L2 distance of word vectors may be employed to cluster the million-level vocabulary into, such as, 200 classes. The classes are used for representing generalized words in the query.

It should be appreciated that the above discussed features for the logistic regression model are illustrative rather than limitative, and according to actual requirements, more or less features mat be used by the logistic regression model.

Input to the diet and product recommendation model may also comprise a user profile 1010 output by a user profile model. The user profile model may be used for predicting gender, age and location information in the user profile from historical queries of the user. The training data may be manually created.

For a gender classification model, the input is <user id, queries> and the output is tags of "male" or "female". A number of clues in the queries can be utilized, such as, "my wife does not do any family works" is likely spoken by a married man, "my husband is quite busy recently" is more frequently spoken by a married woman, etc.

For an age predication model, the input is <user id, queries> and the output is a tag of, e.g., "10+", "20+", "30+", "40+", "50+" or "60+", where "10+" indicates an age between 10 and 20, "20+" indicates an age between 20 and 30, "30+" indicates an age between 30 and 40, and so on. The age prediction model may determine age information based on the queries. For example, if a user says "I am a senior middle school student" in a session, it may be determined that the age of the user is "10+". If a user says "I am already retired" in a session, it may be determined that the user is very likely to be "60+".

For a location detection model, the input is <user id, queries> and the output may be at least one tag of location. The location detection model may determine location information based on the queries. For example, if a user says "Do you have any suggestions on restaurants for working lunch around Ueno?" in a session, it may be determined that the user is working around Ueno in Tokyo.

The above three classification or detection models may be trained based on training data of <user id, queries, target tags>. The features for the training may comprise:

Target product category or company of the query: for example, females may have stronger tendency to domains of cosmetics and their related companies.

Disease keywords included in the user's historical query: for example, man and woman may have shared diseases and gender-sensitive diseases, such as mammary-related diseases for woman and prostate-related diseases for man.

The list of location related words that the user mentioned the most: an existing location lexicon may be used for detecting location related words in the user's queries.

Word ngrams: unigrams and bigrams for words in the query.

Character ngrams: for each word in the query, character ngrams are extracted. For example, 4-grams and 5-grams are used in this model.

Word skip-grams: for all the trigrams and 4-grams in the query, one of the words is replaced by a symbol, such as, "*", to indicate the presence of non-contiguous words.

Brown cluster ngrams: Brown clusters are used for representing words in query, and then unigrams and bigrams are extracted as features.

Part-of-speech (POS) tags: the presence or absence of POS tags is used as binary features.

Social network related words: number of hashtags, emoticons, elongated words, and punctuations in the query are used as features.

Word2vec cluster ngrams: the word2vec tool (Mikolov et al., 2013) may be used for learning 100-dimensional word embedding from a social network dataset. Then, K-means algorithm and L2 distance of word vectors may be employed to cluster the million-level vocabulary into, such as, 200 classes. The classes are used for representing generalized words in the query.

A multiple-class support vector machine (SVM) model may be trained using the above exemplary features. These three models may share similar feature templates. In an implementation, as for the user's health condition or concerned diseases, an existing disease lexicon may be used directly for matching the user's historical queries, and then the health condition or diseases with their mentioned frequencies may be recorded. Moreover, the user profile 1010 may comprise cooking method preference or taste preference of the user, which may also be extracted from the queries.

Input to the diet and product recommendation model may also comprise knowledge graph 1012. The knowledge graph 1012 may be established according to the process 700 in FIG. 7.

Input to the diet and product recommendation model may also comprise a product data set 1014 and keyword-biding data 1016. The product data set 1014 and the keyword-biding data 1016 may be obtained from partner entities 1018. The product data set 1014 may comprise various product related information, such as, product list, service list, brands, prices, promotions, producer names, selling addresses, etc. The keyword-biding data 1016 may comprise keywords customized by the partner entities, categories, prices the partner entities are willing to bid, etc.

Although not shown, input to the diet and product recommendation model may also comprise the user's historical emotions on candidate recommendations that are determined through sentiment analysis. For example, if there is a query "I like to eat fruits" recorded in the session log, this will show a positive opinion by the user on fruits.

The diet and product recommendation model may be constructed by using a LTR model. The diet and product recommendation model may rank available recommendations under a specific query from the user. A GBDT algorithm may be trained for the ranking. In an implementation, the following features may be used for the GBDT algorithm:

Diet intension classification's output

User profile, including information about, such as, gender, age, location, health condition, cooking method preference, taste preference, etc.

User click model's output: such as, the CTR predication of candidate recommendations.

Keyword-bidding data

Word ngrams: unigrams and bigrams for words in the query.

Character ngrams: for each word in the query, character ngrams are extracted. For example, 4-grams and 5-grams are used in this model.

Word skip-grams: for all the trigrams and 4-grams in the query, one of the words is replaced by a symbol, such as, "*", to indicate the presence of non-contiguous words.

Brown cluster ngrams: Brown clusters are used for representing words in query, and then unigrams and bigrams are extracted as features.

Part-of-speech (POS) tags: the presence or absence of POS tags is used as binary features.

Social network related words: number of hashtags, emoticons, elongated words, and punctuations in the query are used as features.

Word2vec cluster ngrams: the word2vec tool (Mikolov et al., 2013) may be used for learning 100-dimensional word embedding from a social network dataset. Then, K-means algorithm and L2 distance of word vectors may be employed to cluster the million-level vocabulary into, such as, 200 classes. The classes are used for representing generalized words in the query.

Knowledge graph's distance of topic words in the query compared with words in the candidate recommendation: for example, "diabetes mellitus" and "non-starchy vegetables" in FIG. 8B may have a distance of 1 since these two entries may be linked together in a tuple.

User's historical emotions on candidate recommendations: for example, if there is a query "I like to eat fruits" in the session log and a current candidate recommendation has a material of "apple", then this candidate recommendation may have a relatively higher chance to be recommended.

It should be appreciated that the above discussed features for the GBDT algorithm are illustrative rather than limitative, and according to actual requirements, more or less features mat be used by the GBDT algorithm.

As mentioned above, a list of candidate recommendations 1020 may be output by the diet and product recommendation model.

A top-ranked candidate recommendation may be provided to the user firstly. Then, it may be determined at 1022 whether a positive feedback is received from the user. Herein, "positive feedback" may refer to, such as, a message from the user indicating that the user likes the recommendation, a click operation by the user on the candidate recommendation, etc. If a positive feedback is received, the process 1000 will be finished at 1026. If a negative feedback is received from the user, such as, a message "I don't like it. Change another one", it may be checked at 1024 whether there are any other remaining candidate recommendations in the list. If yes at 1024, the next top-ranked candidate recommendation is provided to the user, while if no at 1024, the process 1000 will be finished at 1026.

As an alternative way, if no at 1024, the user may be notified that there is no suitable candidate recommendation to the query. Furthermore, a feedback may be generated based on such result and provided to the partner entity supplying the product, such that the partner entity may know there is a possible need to improve its product list or develop new product.

In an implementation, the user's click actions on the respective candidate recommendations may be transferred to the user click model 1006, and accordingly the user click model 1006 may update the user's historical click record. An example of an entry in the historical click record may be the number of positive feedbacks or the number of negative feedbacks from the user on a candidate recommendation.

Figure 11:
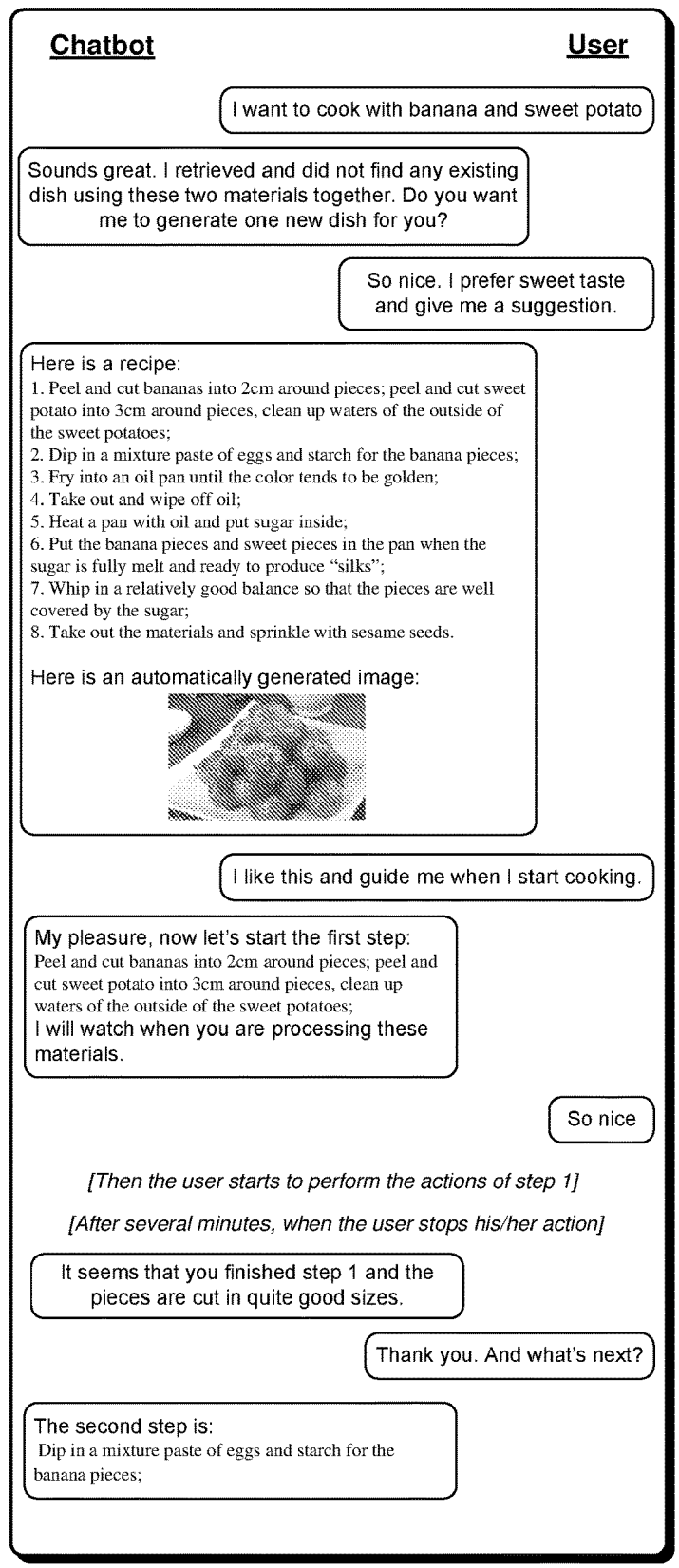
FIG. 11 illustrates an exemplary chat window according to an embodiment.

FIG. 11 illustrates an exemplary chat window 1100 according to an embodiment. The chat window 1100 shows an exemplary procedure for providing diet suggestions including recipe in a session according to the embodiment.

When receiving a message "I want to cook with banana and sweet potato" in the session, the chatbot may determine, based at least on the session and the message, that the diet intention of the user is acquiring recipe recommendation related to banana and sweet potato. The chatbot may extract diet information, such as, cooking ingredients "banana" and "sweet potato", from the message. The chatbot may try to retrieve an existing recipe that is indexed in the database for providing diet suggestions, however in this example, there is no indexed recipe related to both of the cooking ingredients "banana" and "sweet potato". Thus, the chatbot may provide a response to the user, such as "Sounds great. I retrieved and did not find any existing dish using these two materials together. Do you want me to generate one new dish for you?".

When receiving a message "So nice. I prefer sweet taste and give me a suggestion" in the session, the chatbot may determine, based at least on the session and the message, that the diet intention of the user is acquiring recipe recommendation related to banana and sweet potato. The chatbot may further identify a diet requirement, such as, taste preference "sweet taste", based at least on the session and the message. It should be appreciated that in some cases, the chatbot may also identify diet requirement from a user profile of the user which may include taste preference or cooking method preference of the user. Then, based at least on the diet intention, the diet information "banana" and "sweet potato" extracted previously and the diet requirement, the chatbot may obtain a recipe as a diet suggestion, wherein the recipe is newly generated by the chatbot with the cooking ingredients "banana" and "sweet potato" in the taste preference "sweet taste". For example, FIG. 11 shows a recipe in a response generated by the chatbot, which includes 8 cooking steps. Moreover, the chatbot may further provide an image of the dish to the user, which is generated based on the recipe.

When receiving a message "I like this and guide me when I start cooking" in the session, the chatbot may begin to guide the user to cook following the recipe. The chatbot may provide a response, such as, "My pleasure, now let's start the first step: . . . I will watch when you are processing these materials". Meanwhile, the chatbot may monitor the user's actions and cooking status of the cooking ingredients through at least one camera.

When identifying that the user stops his actions and the cooking ingredients are prepared well according to the first step, the chatbot may confirm with the user and start to guide the second step. In this way, the chatbot may finally guide the user to cook a dish based on the recipe.

Figure 12:
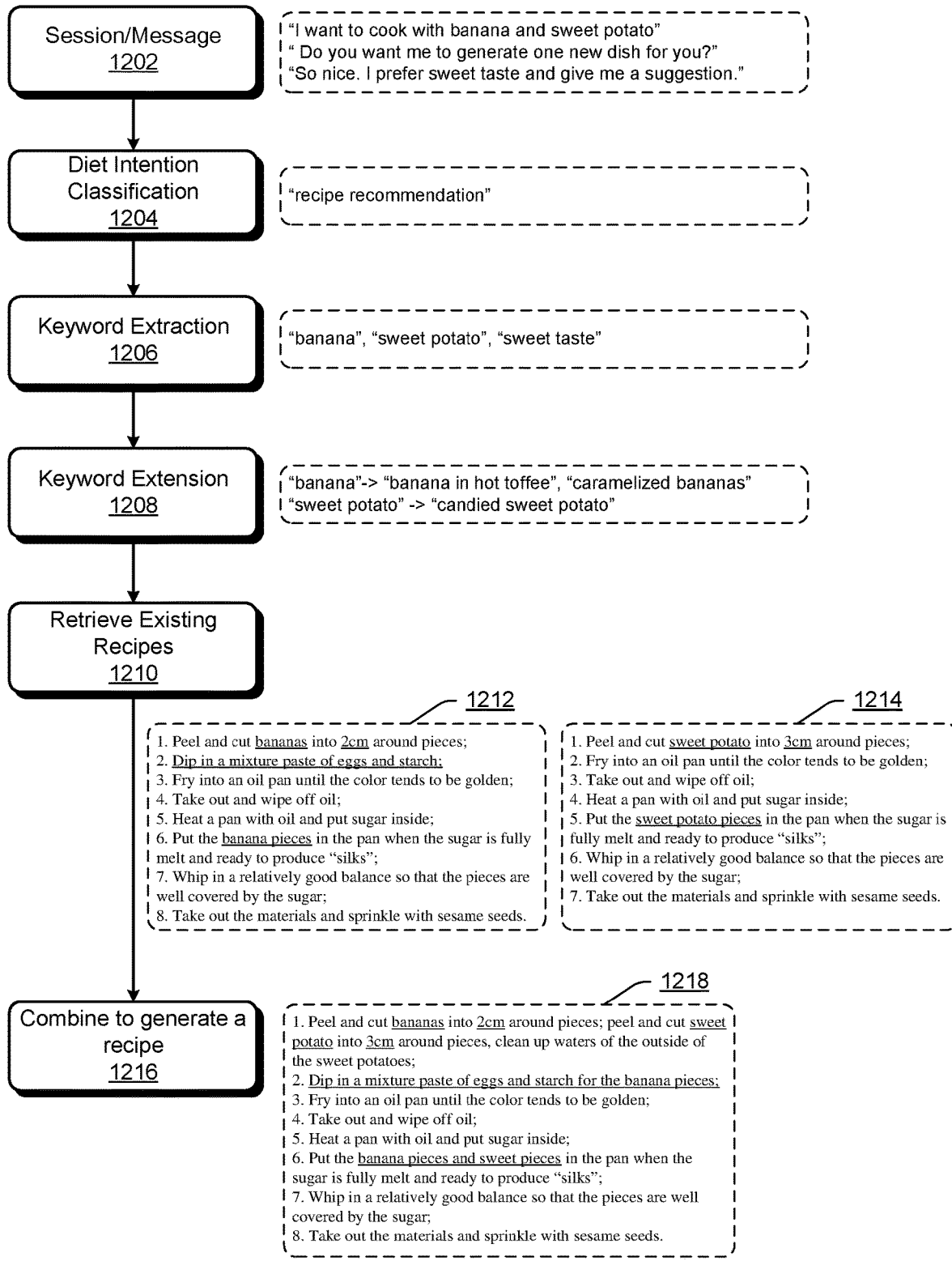
FIG. 12 illustrates an exemplary process for generating a recipe according to an embodiment.

FIG. 12 illustrates an exemplary process 1200 for generating a recipe according to an embodiment.

At 1202, a current session and/or at least one latest message may be obtained, such as "I want to cook with banana and sweet potato", "Do you want me to generate one new dish for you?", "So nice. I prefer sweet taste and give me a suggestion", etc. in FIG. 11.

At 1204, diet intention classification may be performed in a way as discussed above in connection with the operation at 530 in FIG. 5. In the scenario of FIG. 12, the diet intention of the user may be determined as recipe recommendation.

At 1206, keywords may be extracted from the current session and/or the at least one message. The keywords may comprise diet information, such as the cooking ingredients "banana" and "sweet potato", and diet requirement, such as the taste preference "sweet taste".

At 1208, semantical keyword extension may be performed on the extracted keywords. In an implementation, a pre-established topic knowledge graph may be adopted for the keyword extension. For example, the keyword "banana" may be semantically extended to "banana in hot toffee", "caramelized bananas", etc., and the keyword "sweet potato" may be semantically extended to "candied sweet potato", etc.

At 1210, existing or indexed recipes may be retrieved based on the extended keywords. For example, an existing recipe 1212 for "caramelized bananas" and an existing recipe 1214 for "candied sweet potato" may be retrieved. Various existing recipes may be collected from the network by the chatbot previously.

At 1216, the retrieved existing recipes 1212 and 1214 may be combined to generate a new recipe 1218.

In an implementation, steps in recipes may be divided into several phases, e.g., including: phase 1 "ingredient preparing and pre-processing"; phase 2 "cooking major ingredients", wherein the major ingredients may be, such as, banana and sweet potato; phase 3 "cooking assistant ingredients", wherein the assistant ingredients may be, such as, sugar; phase 4 "cooking both the major ingredients and the assistant ingredients"; phase 5 "post-processing"; and so on. The above phases are exemplary, and according to actual requirements, more or less phases may be divided for recipes.

Steps 1 to 2 in the recipe 1212 and step 1 in the recipe 1214 may correspond to phase 1, steps 3 to 4 in the recipe 1212 and steps 2 to 3 in the recipe 1214 may correspond to phase 2, step 5 in the recipe 1212 and step 4 in the recipe 1214 may correspond to phase 3, steps 6 to 7 in the recipe 1212 and steps 5 to 6 in the recipe 1214 may correspond to phase 4, step 8 in the recipe 1212 and step 7 in the recipe 1214 may correspond to phase 5.

Support vector machines (SVMs) may be used for training a "phase" classification model which may use, such as, tri-gram character and bi-gram word features of the recipes collected from the network. Moreover, the 5 phases may be manually annotated to the recipes for building training data.

In an implementation, similar steps in different recipes may be linked together. If sentences of two steps are quite similar except named entities, then a simple combination of linking these named entities together may be made, so as to obtain a new sentence that exactly indicates processing these named entities together. For example, step 6 in the recipe 1212 and step 5 in the recipe 1214 are similar except the different named entities "banana pieces" and "sweet potato pieces". These two steps may be combined together as step 6 in the new recipe 1218 which indicates processing "banana pieces" and "sweet potato pieces" together.

In an implementation, different steps or phases may be identified from the recipes. When one step is special for a recipe, such as step 2 in the recipe 1212, this step may be simply inserted in a corresponding phase of the new recipe, such as phase 1 "ingredient preparing and pre-processing" of the new recipe 1218.

Figure 13:
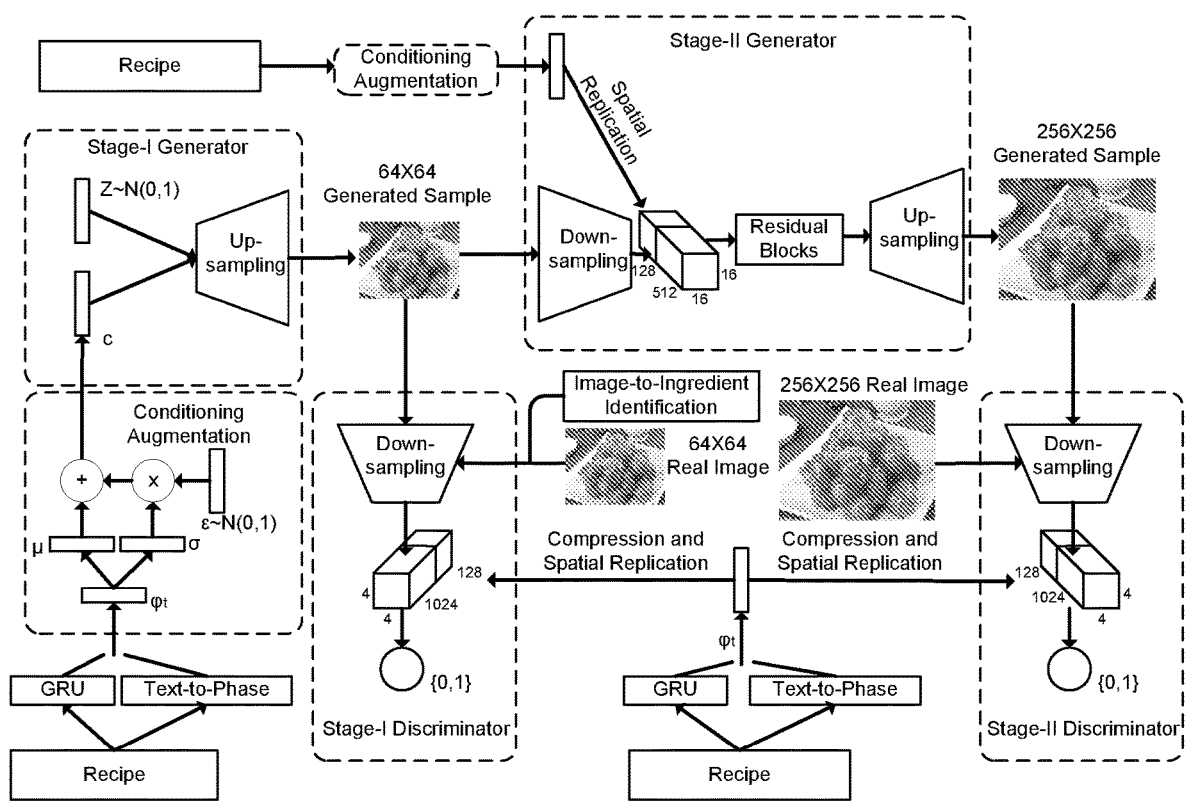
FIG. 13 illustrates an exemplary text-to-image generation model according to an embodiment.

FIG. 13 illustrates an exemplary text-to-image generation model 1300 according to an embodiment. The model 1300 may be used for generating an image of a dish based on a corresponding recipe. The generated image may be provided to a user such that the user may have an intuitive recognition on a recipe suggested by the chatbot.

Generative Adversarial Network (GAN) structure may be adopted in the whole generation process by the model 1300. The GAN structure includes two generators and two discriminators, denoted as Stage-I generator, Stage-I discriminator, Stage-II generator, and Stage-II discriminator. The Stage-I generator draws a low-resolution image by sketching rough shapes and basic colors of objects from a given text and then painting background color from a random noise vector. Then, the Stage-II generator generates a high-resolution image with photo-realistic details by conditioning on both the result of Stage-I and the textual input again.

In a traditional GAN, training procedure is similar to a two-player min-max game taking the following objective function for optimization:

$$\min_G \max_D V(D, G) = \mathbb{E}_{x \sim p_{data}}[\log D(x)] + \mathbb{E}_{z \sim p_z}[\log(1 - D(G(z)))],$$

Equation (5)

where D and G denote the discriminator and the generator respectively. G is optimized to re-produce the true data distribution $p_{data}$ by generating images that are difficult for the discriminator D to distinguish from real images. At the same time, D is optimized to distinguish real images from $p_{data}$ and synthetic images that are generated from G.

In Equation (5), x is a real image following the true data distribution $p_{data}$, z is a noise vector sampled from distribution $p_z$, such as, a uniform distribution, or a one-dimension/multiple-dimension Gaussian distribution. D(x) is the probability that D outputs by giving x as D's input and D(G(z)) is the probability that D assigns to z, which is generated by G. The task of D is to maximize the score in V(D, G) which is to "let real data to be as close to 1 as possible and let synthetic data to be as close to 0 as possible". Furthermore, the task of G is to "cheat" D as much as possible, that is, to minimum D's benefit.

It is easy to extend both G and D by appending additional conditional variables c, yielding G(x, c) and D(x, c). This formulation allows G to generate images conditioned on variables c. For example, the textual input of the recipe 1218 in FIG. 12 is one type of c.

As shown in FIG. 13, the conditioning text description t is firstly encoded by an encoder, yielding a text embedding $\emptyset_t$. GRU and a fine-grained text-to-emotion network may be used for obtaining this text embedding $\emptyset_t = [GRU_t, emotion_t]$. One difficulty here is that latent space conditioned on a text embedding vector usually has a high dimension. With limited amount of data, it usually causes discontinuity in the latent data manifold, which is harmful for learning the generator. As shown in FIG. 13, a conditioning augmentation module may be used for producing more conditioning variables for the generator. That is, more latent variables are sampled from an independent Gaussian distribution N ($\mu(\emptyset_t)$, $\Sigma(\emptyset_t)$), where the mean $\mu(\emptyset_t)$ and diagonal co-variance matrix $\Sigma(\emptyset_t)$ are functions of the text embedding $\emptyset_t$. This will bring more training pairs given a small number of image-text pairs, since more sentences are introduced, which share a similar semantic meaning as compared with the original textual input. Assuming the original textual input is "that girl is about 4 years old, Japan-US half, with pink cloth and sweet smile", the introduced more sentences may include sentences like "that 4-years-old girl is a Japan-US half, dresses pink shirts and laughs"). The standard Gaussian distribution, N (0, 1), may be used for enforcing the smoothness over the conditioning manifold to avoid overfitting. KL divergence may be used here for computing:

$$D_{KL}(N(\mu(\emptyset_t), \Sigma(\emptyset_t)) \| N(0, I))$$

Equation (6)

The output of "conditioning augmentation" is c, which is sent to Stage-I generator. Generally, Stage-I GAN trains $D_0$ and $G_0$ by maximizing $L_{D0}$ and minimizing $L_{G0}$:

$$\mathcal{L}_{D_0} = \mathbb{E}_{(I_0, t) \sim p_{data}}[\log D_0(I_0, \varphi_t)] + \mathbb{E}_{z \sim p_z, t \sim p_{data}}[\log(1 - D_0(G_0(z, c_0), \varphi_t))],$$

$$\mathcal{L}_{G_0} = \mathbb{E}_{z \sim p_z, t \sim p_{data}}[\log(1 - D_0(G_0(z, c_0), \varphi_t))] + \lambda D_{KL}(\mathcal{N}(\mu_0(\varphi_t), \Sigma_0(\varphi_t)) \| \mathcal{N}(0, I)),$$

Equation (7)

Here, the text description t and the real image $I_0$, which is a combination of the image vector and the emotion vector of the image, alike [$I_{image}$, emotion vector], are from the true data distribution $p_{data}$. As mentioned above, z is a noisy vector. $\lambda$ is a regularization parameter that controls the balance between the two terms in $L_{G0}$. For example, $\lambda=1$ may be used for this model. Gaussian conditioning variables $c_0$ are sampled from N ($\mu_0(\emptyset_t)$, $\Sigma_0(\emptyset_t)$) to reflect the text description.

For Stage-I generator, the emotional text embedding $\emptyset_t$ is fed into a fully connected layer to generate $\mu_0$ and $\sigma_0$ for Gaussian distribution N ($\mu_0(\emptyset_t)$, $\Sigma_0(\emptyset_t)$), where $\sigma_0$ are values in the diagonal of $\Sigma_0$). Vector $c_0$ is computed by $c_0 = \mu_0 + \sigma_0 * e$, where * is element-wise multiplication and e follows N (0, 1). Then, $c_0$ is concatenated with a $N_z$-dimension noise vector to generate a $W_0 \times H_0$ image by a series of up-sampling blocks.

For the discriminator, the text embedding $\emptyset_t$ is firstly compressed to $N_d$ dimensions using a fully connected layer, and then spatially replicated to form a $M_d \times M_d \times N_d$ tensor. Meanwhile, the image is fed through a series of down-sampling blocks until it has $M_d \times M_d$ spatial dimension. Then, the image filter map is concatenated along the channel dimension with the text tensor. The resulting tensor is further fed to a 1×1 convolutional layer to jointly learn features across the image and the text. Finally, a fully connected layer with one node is used for producing the decision score.

Stage-II GAN may be constructed in a similar way as Stage-I GAN discussed above. Stage-II GAN is built upon Stage-I GAN to generate photo-realistic high-resolution images. Stage-II GAN conditions not only on low resolution images generated by the previous stage, but also on the text embedding again to correct defects in Stage-I's results and encourage the model to extract previously and possibly ignored information in the text to generate more photo-realistic details.

Conditioning on the low-resolution sample $s_0$ and Gaussian latent variables c, the discriminator D and generator G in Stage-II GAN is trained by alternatively maximizing $L_D$ and minimizing $L_G$:

$$\mathcal{L}_D = \mathbb{E}_{(I,t)\sim p_{data}}[\log D(I,\varphi_t)] + \mathbb{E}_{x \sim p G_0, t \sim p_{data}}[\log(1-D(G(s_0,c),\varphi_t))],$$

$$\mathcal{L}_G = \mathbb{E}_{z_0 \sim p G_0, t \sim p_{data}}[\log(1-D(G(s_0,c),\varphi_t))] + \lambda D_{KL}(\mathcal{N}(\mu(\varphi_t), \Sigma(\varphi_t)) \| \mathcal{N}(0,1))$$

Equation (8)

Here $s_0 = G_0(z, c_0)$ is generated by Stage-I GAN. The "residual blocks" in FIG. 13 uses a residual function and blocks same as the existing ResNet.

One extension to the model 1300 is to consider a sequence of GANs for coarse-to-fine text-to-image generation. With more GANs, it can be supposed to make use of GAN blocks to take care of more details and to generate higher resolution images. For example, Stage-III GAN and more stage GANs may be extended in FIG. 13 in a similar way as the extension from Stage-I to Stage-II.

According to the embodiments of the present disclosure, the chatbot may perform video capture on a cooking video stream to obtain corresponding texts and voices. For example, through the video capture, a set of texts may be generated to describe what is playing in the cooking video, such as textual description of actions of the person in the video, textual description of cooking status of ingredients in the video, etc. Finally, the set of texts may form a recipe which can be provided to a user as a diet suggestion. Moreover, voices may be generated based on the set of texts through various text-to-speech techniques, and thus voice guidance may be prepared for the recipe formed by the set of texts. The cooking video stream may be an online video stream or an offline prepared video file.

Figure 14:
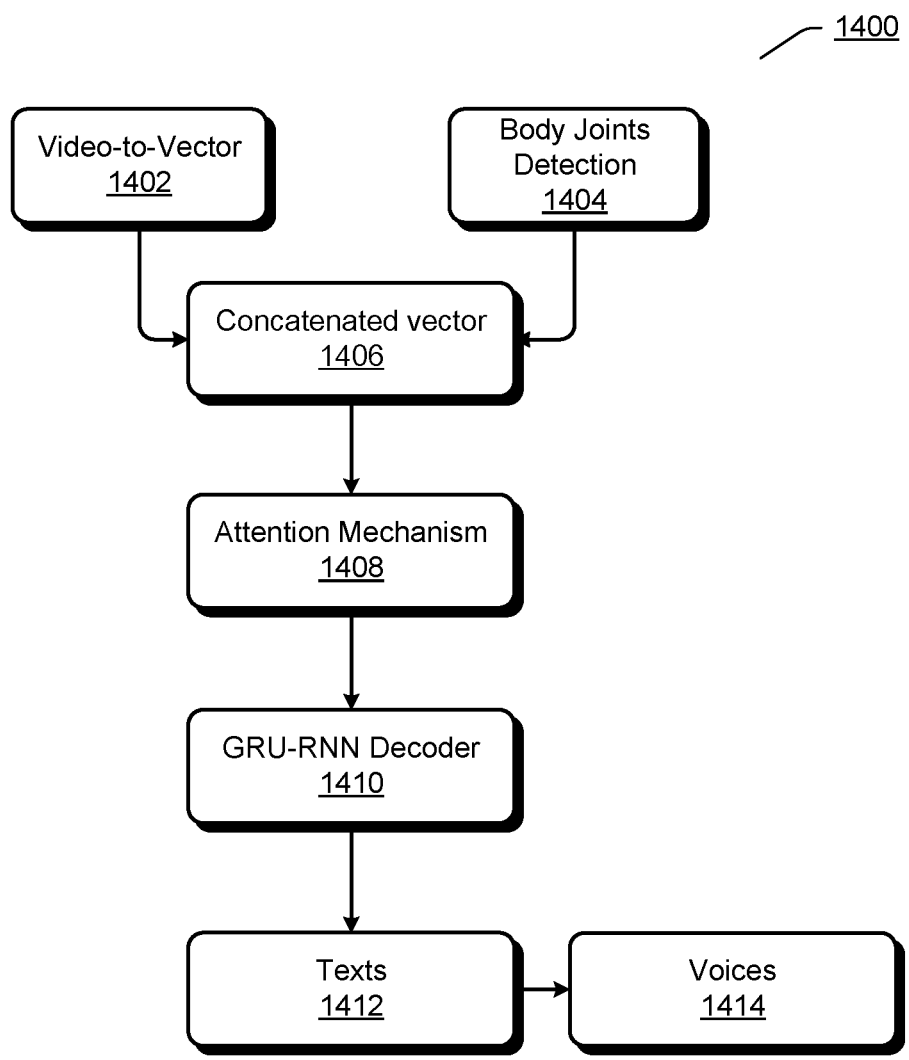
FIG. 14 illustrates an exemplary process for video capture according to an embodiment.

FIG. 14 illustrates an exemplary process 1400 for video capture according to an embodiment. The video capture may be based on a video-to-text style encoding-decoding algorithm, wherein a 2D/3D Convolutional Neural Network (CNN) may be taken as the encoding part, and a GRU style RNN network may be taken as the decoding part.

At 1402, a video-to-vector encoding process may be performed, through which vector representation of an input video may be obtained. In an implementation, frames of the input video may be encoded under 2D CNN, such as, AlexNet, GoogleNet, VGG, ResNet, etc., and clips of the input video may be encoded by convolutional 3D filters in a 3D CNN. The outputs of the 2D CNN and 3D CNN may be combined to obtain vector representation of the input video.

Figure 15A:
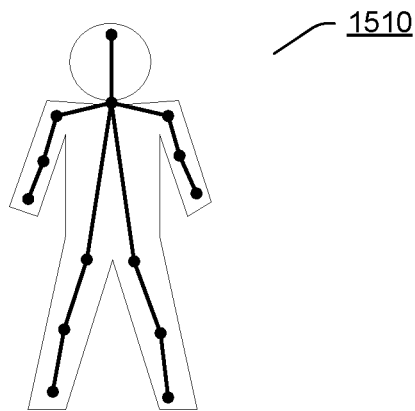
FIG. 15A illustrates an exemplary representation of body joints according to an embodiment.

At 1404, body joints detection may be performed so as to identify actions of a user in the input video. FIG. 15A illustrates an exemplary representation 1510 of body joints according to an embodiment. Basically, there are 14 important body joints for presenting or identifying a full body figure. A total of 14 read points are shown in FIG. 15A for representing body joints of real body parts, such as, top of head, bottom of head, left and right shoulder points, two elbows, two arms, two hip points, two knees, and two ankles. It should be appreciated that the 14 body joints are not necessarily appearing all in a given photo. For example, less than 14 body joints may be found in a half body photo, and for a side profile of a body, most of the symmetric body joints are identical, such as two shoulder points become to be one.

Figure 15B:
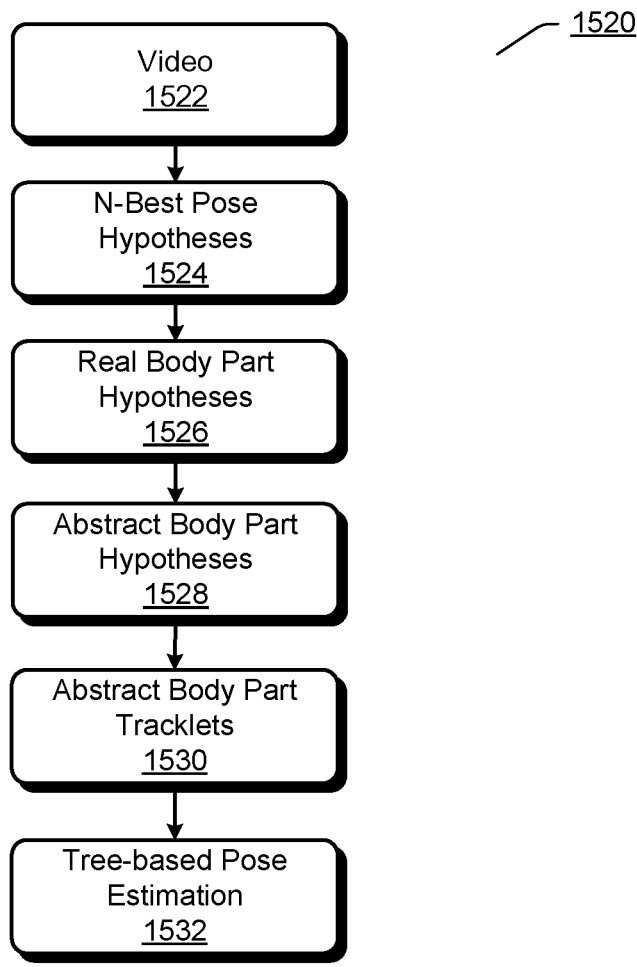
FIG. 15B illustrates an exemplary process for body joints detection according to an embodiment.

A deep learning model may be trained for automatically detecting the 14 body joints from video streams. FIG. 15B illustrates an exemplary process 1520 for body joints detection according to an embodiment. The body joints detection may also be referred to as body pose detection. At 1522, original video frames may be input. At 1524, an existing N-Best method may be employed to generate a set of diverse pose hypotheses for each single frame. At 1526, according to the N-best pose hypotheses generated at 1524, real body part hypotheses are generated for each body part in each frame, and propagated to adjacent frames. At 1528, real body parts are combined into abstract body parts, and the real body part hypotheses are also combined into abstract body part hypotheses, in order to remove intra-frame simple cycles. At 1530, according to the abstract body part hypotheses generated at 1528, tracklets are generated for the abstract body parts including single body parts and coupled body parts. At 1532, tree-based pose estimation is made. For example, a pose hypotheses graph may be built in which each node is a tracklet corresponding to an abstract body part, and the best pose estimation may be obtained by selecting the best hypothesis for the body part from the pose hypotheses graph.

At 1406, the vector representation of the input video generated at 1402 and a vector representation for body joints detection at 1404 may be combined to obtain a concatenated vector.

The concatenated vector may be provided to a GRU-RNN decoder 1410 through an attention mechanism 1408. The GRU-RNN decoder 1410 may be configured for decoding the concatenated vector into texts 1412. Accordingly, a conversion from the input video to the texts is achieved.

In an implementation, the process 1400 may further comprise transforming the texts 1412 to voices 1414 through various text-to-speech techniques.

Figure 16:
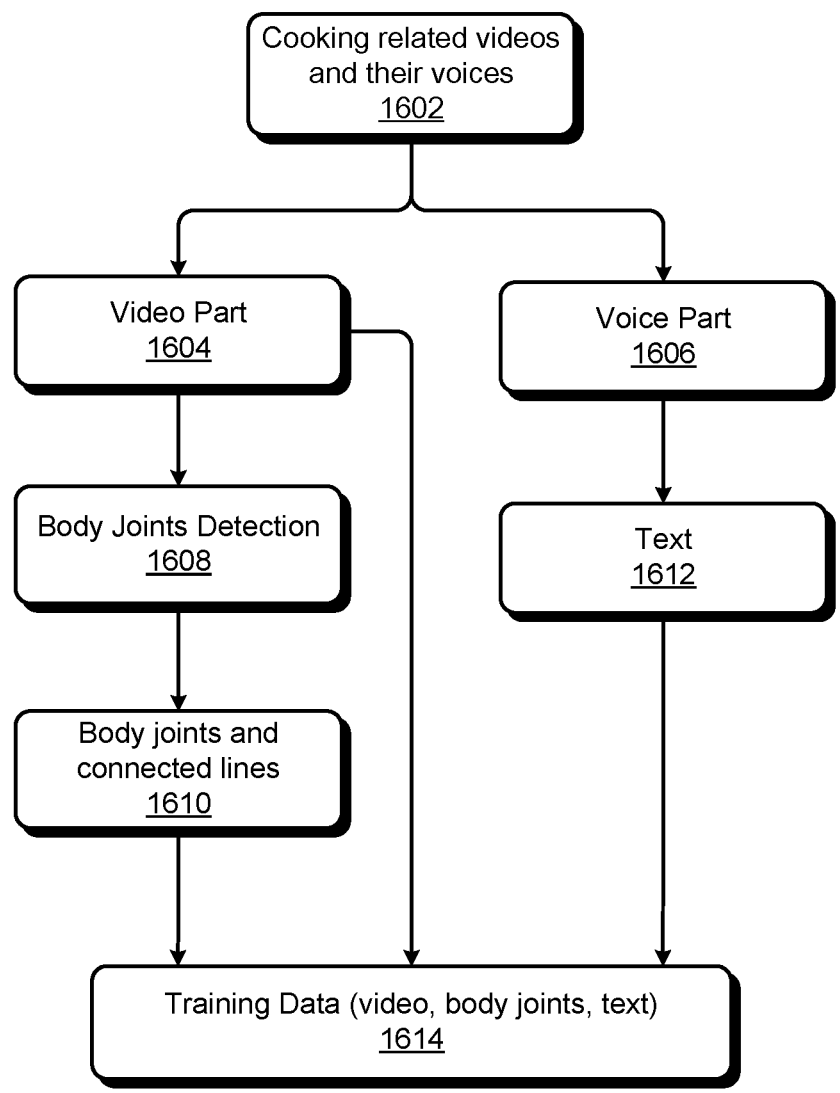
FIG. 16 illustrates an exemplary process for obtaining training data for video capture according to an embodiment.

FIG. 16 illustrates an exemplary process 1600 for obtaining training data for video capture according to an embodiment.

At 1602, cooking related videos and corresponding voices may be obtained. For example, the videos and voices may be collected from cooking websites, TV shows, etc. Then, video part 1604 and voice part 1606 may be separated from the videos and corresponding voices obtained at 1602 respectively.

For the video part 1604, body joints detection may be performed at 1608, so as to identify body joints in the video part and obtain connected lines among adjacent body joints.

For the voice part 1606, a voice-to-text conversion may be performed to obtain a corresponding text 1612.

At 1614, training data may be obtained with the input video, the body joints identified at 1610 and the text 1612, and may be denoted in a form of (video, body joints, text). The training data may be used for training the video capture process according to the embodiments of the present disclosure.

As discussed above, the chatbot according to the embodiments of the present disclosure may guide the user to cook following a recipe. In an aspect, the body joints detection method discussed in connection with FIG. 15A and FIG. 15B may be adopted in cooking guidance by the chatbot. For example, when the chatbot is integrated in a terminal device, such as, a family-oriented intelligent voice box, cameras of the terminal device may be used for shooting a video in real time when the user is cooking under the guidance of the chatbot, and through the body joints detection, the user's actions in the video may be captured and identified. Thus, the chatbot may know whether the user is cooking in an appropriate way following the recipe. In another aspect, the chatbot may identify, from the video shot by the cameras, cooking status of ingredients, such as, identifying the prepared size of an ingredient, whether an ingredient has been cooked well, etc. In another aspect, during the cooking guidance, the chatbot may generate voices based on a recipe, or use the voices 1414 in FIG. 14 directly if the voices 1414 correspond to the recipe.

Figure 17:
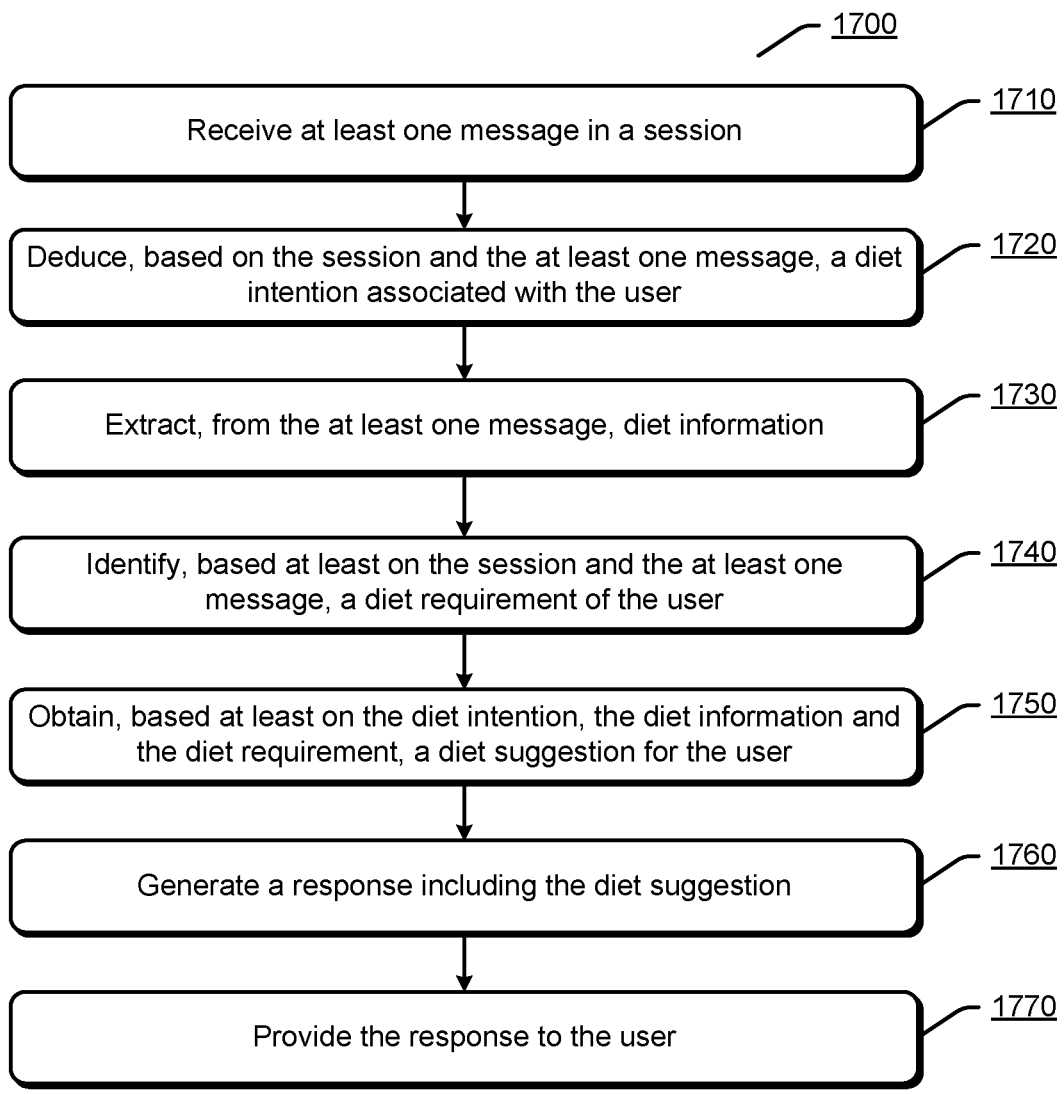
FIG. 17 illustrates a flowchart of an exemplary method for providing diet assistance to a user in a session according to an embodiment.

FIG. 17 illustrates a flowchart of an exemplary method 1700 for providing diet assistance to a user in a session according to an embodiment.

At 1710, at least one message may be received in the session, the session being between the user and an electronic conversational agent.

At 1720, a diet intention associated with the user may be deduced based on the session and the at least one message.

At 1730, diet information may be extracted from the at least one message.

At 1740, a diet requirement of the user may be identified based at least on the session and the at least one message.

At 1750, a diet suggestion for the user may be obtained based at least on the diet intention, the diet information and the diet requirement.

At 1760, a response including the diet suggestion may be generated.

At 1770, the response may be provided to the user.

In an implementation, the diet intention may indicate recipe recommendation; the diet information may include at least one cooking ingredient; the diet requirement may include at least one of cooking method preference and taste preference; and the diet suggestion may include a recipe.

The identifying the diet requirement may comprise at least one of: extracting, from the session and the at least one message, the at least one of cooking method preference and taste preference; and retrieving, from a user profile, the at least one of cooking method preference and taste preference, the user profile being established based at least on the session and the at least one message.

The obtaining the diet suggestion may comprise: retrieving at least one indexed recipe, the at least one indexed recipe being related to the at least one cooking ingredient and the at least one of cooking method preference and taste preference.

The obtaining the diet suggestion may comprise: semantically extending the at least one cooking ingredient to obtain at least one extended cooking ingredient; retrieving at least one indexed recipe based on the at least one extended cooking ingredient and the at least one of cooking method preference and taste preference; and generating a recipe based on the at least one indexed recipe, the generated recipe being related to the at least one cooking ingredient and the at least one of cooking method preference and taste preference.

The method 1700 may further comprise: guiding, based at least on the user's actions and/or cooking status of the at least one cooking ingredient, the user to cook following the recipe.

In an implementation, the diet intention may indicate at least one of diet recommendation and product recommendation; the diet information may include at least one of food type, food name, dish name and concerned disease; the diet requirement may include health condition of the user; and the diet suggestion may include at least one of food name, dish name and product information.

The identifying the diet requirement may comprise at least one of: extracting the health condition from the session and the at least one message; and retrieving the health condition from a user profile, the user profile being established based at least on the session and the at least one message.

The obtaining the diet suggestion may comprise: ranking a plurality of candidate recommendations based on at least one of a user profile, click-through-rates of the plurality of candidate recommendations, keyword-bidding information of the plurality of candidate recommendations, a knowledge graph related to diet and/or disease, historical emotions on the plurality of candidate recommendations, and a product data set; and selecting one or more top-ranked candidate recommendations as the diet suggestion.

In an implementation, the diet intention may indicate diet knowledge acquirement; the diet information may include at least one of food type, food name, dish name and concerned disease; the diet requirement may include health condition of the user; and the diet suggestion may include diet knowledge.

The obtaining the diet suggestion may comprise: retrieving, based at least on the diet intention, the diet information and the diet requirement, the diet knowledge from a knowledge graph or a knowledge question-answer pair set.

In an implementation, the at least one message may comprise at least one of text message, speech message and image message.

It should be appreciated that the method 1700 may further comprise any steps/processes for providing diet assistance to a user in a session according to the embodiments of the present disclosure as mentioned above.

Figure 18:
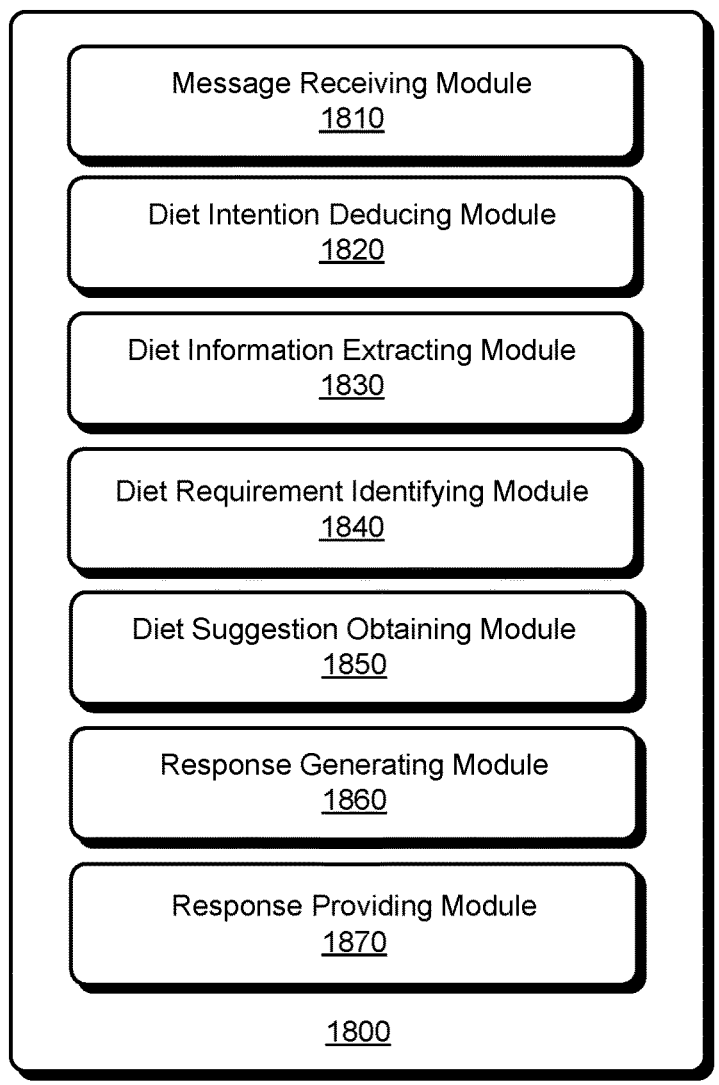
FIG. 18 illustrates an exemplary apparatus for providing diet assistance to a user in a session according to an embodiment.

FIG. 18 illustrates an exemplary apparatus 1800 for providing diet assistance to a user in a session according to an embodiment.

The apparatus 1800 may comprise: a message receiving module 1810, for receiving at least one message in the session, the session being between the user and an electronic conversational agent; a diet intention deducing module 1820, for deducing, based on the session and the at least one message, a diet intention associated with the user; a diet information extracting module 1830, for extracting, from the at least one message, diet information; a diet requirement identifying module 1840, for identifying, based at least on the session and the at least one message, a diet requirement of the user; a diet suggestion obtaining module 1850, for obtaining, based at least on the diet intention, the diet information and the diet requirement, a diet suggestion for the user; a response generating module 1860, for generating a response including the diet suggestion; and a response providing module 1870, for providing the response to the user.

In an implementation, the diet intention may indicate recipe recommendation; the diet information may include at least one cooking ingredient; the diet requirement may include at least one of cooking method preference and taste preference; and the diet suggestion may include a recipe.

The diet requirement identifying module 1840 may be further for at least one of: extracting, from the session and the at least one message, the at least one of cooking method preference and taste preference; and retrieving, from a user profile, the at least one of cooking method preference and taste preference, the user profile being established based at least on the session and the at least one message.

The diet suggestion obtaining module 1850 may be further for: semantically extending the at least one cooking ingredient to obtain at least one extended cooking ingredient; retrieving at least one indexed recipe based on the at least one extended cooking ingredient and the at least one of cooking method preference and taste preference; and generating a recipe based on the at least one indexed recipe, the generated recipe being related to the at least one cooking ingredient and the at least one of cooking method preference and taste preference.

The apparatus 1800 may further comprise: a cooking guiding module, for guiding, based at least on the user's actions and/or cooking status of the at least one cooking ingredient, the user to cook following the recipe.

In an implementation, the diet intention may indicate at least one of diet recommendation and product recommendation; the diet information may include at least one of food type, food name, dish name and concerned disease; the diet requirement may include health condition of the user; and the diet suggestion may include at least one of food name, dish name and product information.

In an implementation, the diet intention may indicate diet knowledge acquisition; the diet information may include at least one of food type, food name, dish name and concerned disease; the diet requirement may include health condition of the user; and the diet suggestion may include diet knowledge.

Moreover, the apparatus 1800 may also comprise any other modules configured for providing diet assistance to a user in a session according to the embodiments of the present disclosure as mentioned above.

Figure 19:
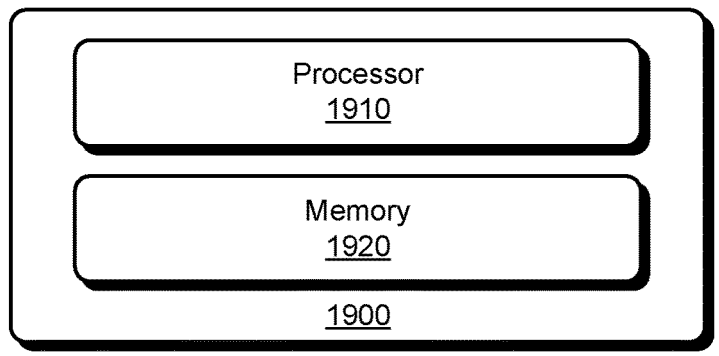
FIG. 19 illustrates an exemplary apparatus for providing diet assistance to a user in a session according to an embodiment.

FIG. 19 illustrates an exemplary apparatus 1900 for providing diet assistance to a user in a session according to an embodiment.

The apparatus 1900 may comprise one or more processors 1910 and a memory 1920 storing computer-executable instructions. When executing the computer-executable instructions, the one or more processors 1910 may: receive at least one message in the session, the session being between the user and an electronic conversational agent; deduce, based on the session and the at least one message, a diet intention associated with the user; extract, from the at least one message, diet information; identify, based at least on the session and the at least one message, a diet requirement of the user; obtain, based at least on the diet intention, the diet information and the diet requirement, a diet suggestion for the user; generate a response including the diet suggestion; and provide the response to the user.

The embodiments of the present disclosure may be embodied in a non-transitory computer-readable medium. The non-transitory computer-readable medium may comprise instructions that, when executed, cause one or more processors to perform any operations of the methods for providing diet assistance to a user in a session according to the embodiments of the present disclosure as mentioned above.

It should be appreciated that all the operations in the methods described above are merely exemplary, and the present disclosure is not limited to any operations in the methods or sequence orders of these operations, and should cover all other equivalents under the same or similar concepts.

It should also be appreciated that all the modules in the apparatuses described above may be implemented in various approaches. These modules may be implemented as hardware, software, or a combination thereof. Moreover, any of these modules may be further functionally divided into sub-modules or combined together.

Processors have been described in connection with various apparatuses and methods. These processors may be implemented using electronic hardware, computer software, or any combination thereof. Whether such processors are implemented as hardware or software will depend upon the particular application and overall design constraints imposed on the system. By way of example, a processor, any portion of a processor, or any combination of processors presented in the present disclosure may be implemented with a microprocessor, microcontroller, digital signal processor (DSP), a field-programmable gate array (FPGA), a programmable logic device (PLD), a state machine, gated logic, discrete hardware circuits, and other suitable processing components configured to perform the various functions described throughout the present disclosure. The functionality of a processor, any portion of a processor, or any combination of processors presented in the present disclosure may be implemented with software being executed by a microprocessor, microcontroller, DSP, or other suitable platform.

Software shall be construed broadly to mean instructions, instruction sets, code, code segments, program code, programs, subprograms, software modules, applications, software applications, software packages, routines, subroutines, objects, threads of execution, procedures, functions, etc. The software may reside on a computer-readable medium. A computer-readable medium may include, by way of example, memory such as a magnetic storage device (e.g., hard disk, floppy disk, magnetic strip), an optical disk, a smart card, a flash memory device, random access memory (RAM), read only memory (ROM), programmable ROM (PROM), erasable PROM (EPROM), electrically erasable PROM (EEPROM), a register, or a removable disk. Although memory is shown separate from the processors in the various aspects presented throughout the present disclosure, the memory may be internal to the processors, e.g., cache or register.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein. All structural and functional equivalents to the elements of the various aspects described throughout the present disclosure that are known or later come to be known to those of ordinary skill in the art are expressly incorporated herein by reference and are intended to be encompassed by the claims.

What is claimed is:

1. A method for providing diet assistance to a user in a chatbot session, the method comprising:
receiving at least one message in the chatbot session, the chatbot session being between the user and an electronic conversational agent;
establishing a user profile based on the session and the at least one message, the user profile indicating at least on cooking method preference and at least one taste preference;
receiving user profile information of a user profile of the user;
training a support vector machine model (SVM) model to determine a relationship between (i) the at least one message and the user profile information and (ii) a diet intention resulting in a trained SVM model;
operating the trained SVM model based on the session, the user profile information, and the at least one message resulting in the diet intention associated with the user;
extracting, from the at least one message, diet information;

identifying, based on at least one of the session, the user profile information, or the at least one message, a diet requirement of the user;

obtaining, based at least on the diet intention, the diet information and the diet requirement, a diet suggestion for the user;

generating a response including the diet suggestion; and providing the response to the user.

2. The method of claim 1, wherein the diet intention indicates recipe recommendation;

the diet information includes at least one cooking ingredient;

the diet requirement includes at least one of cooking method preference and taste preference; and the diet suggestion includes a recipe.

3. The method of claim 2, wherein the identifying the diet requirement comprises at least one of:

extracting, from the session and the at least one message, the at least one of cooking method preference and taste preference; and retrieving, from a user profile, the at least one of cooking method preference and taste preference, the user profile being established based at least on the session and the at least one message.

4. The method of claim 2, wherein the obtaining the diet suggestion comprises:

retrieving at least one indexed recipe, the at least one indexed recipe being related to the at least one cooking ingredient and the at least one of cooking method preference and taste preference.

5. The method of claim 2, wherein the obtaining the diet suggestion comprises:

semantically extending the at least one cooking ingredient to obtain at least one extended cooking ingredient;

retrieving at least one indexed recipe based on the at least one extended cooking ingredient and the at least one of cooking method preference and taste preference; and generating a recipe based on the at least one indexed recipe, the generated recipe being related to the at least one cooking ingredient and the at least one of cooking method preference and taste preference.

6. The method of claim 2, further comprising:

guiding, based at least on the user's actions and/or cooking status of the at least one cooking ingredient, the user to cook following the recipe.

7. The method of claim 1, wherein the diet intention indicates at least one of diet recommendation and product recommendation;

the diet information includes at least one of food type, food name, dish name and concerned disease;

the diet requirement includes health condition of the user; and the diet suggestion includes at least one of food name, dish name and product information.

8. The method of claim 7, wherein the identifying the diet requirement comprises at least one of:

extracting the health condition from the session and the at least one message; and retrieving the health condition from a user profile, the user profile being established based at least on the session and the at least one message.

9. The method of claim 7, wherein the obtaining the diet suggestion comprises:

ranking a plurality of candidate recommendations based on at least one of: a user profile, click-through-rates of the plurality of candidate recommendations, keyword-bidding information of the plurality of candidate recommendations, a knowledge graph related to diet and/or disease, historical emotions on the plurality of candidate recommendations, and a product data set; and selecting one or more top-ranked candidate recommendations as the diet suggestion.

10. The method of claim 1, wherein the diet intention indicates diet knowledge acquirement;

the diet information includes at least one of food type, food name, dish name and concerned disease;

the diet requirement includes health condition of the user; and the diet suggestion includes diet knowledge.

11. The method of claim 10, wherein the obtaining the diet suggestion comprises:

retrieving, based at least on the diet intention, the diet information and the diet requirement, the diet knowledge from a knowledge graph or a knowledge question-answer pair set.

12. The method of claim 1, wherein the at least one message comprises at least one of text message, speech message and image message.

13. An apparatus for providing diet assistance to a user in a chatbot session, the apparatus comprising:

one or more processors; and a memory storing computer-executable instructions that, when executed, cause the one or more processors to:

receive at least one message in the chatbot session, the chatbot session being between the user and an electronic conversational agent;

establishing a user profile based on the session and the at least one message, the user profile indicating at least on cooking method preference and at least one taste preference;

receiving user profile information of a user profile of the user;

training a support vector machine model (SVM) model to determine a relationship between (i) the at least one message and the user profile information and (ii) a diet intention resulting in a trained SVM model;

operating the trained SVM model, based on the session, the user profile information, and the at least one message resulting in the diet intention associated with the user;

extract, from the at least one message, diet information;

identify, based on at least one of the session, the user profile information, or the at least one message, a diet requirement of the user;

obtain, based at least on the diet intention, the diet information and the diet requirement, a diet suggestion for the user;

generate a response including the diet suggestion; and provide the response to the user.

14. The apparatus of claim 13, wherein the diet intention indicates recipe recommendation;

the diet information includes at least one cooking ingredient;

the diet requirement includes at least one of cooking method preference and taste: preference; and the diet suggestion includes a recipe.

15. The apparatus of claim 14, wherein the instructions further cause the one or more processors to:

extract, from the session and the at least one message, the at least one of cooking method preference and taste preference; and retrieve, from a user profile, the at least one of cooking method preference and taste preference, the user profile being established based at least on the session and the at least one message.

16. The apparatus of claim 14, wherein the instructions further cause the one or more processors to:
   semantically extend the at least one cooking ingredient to obtain at least one extended cooking ingredient;
   retrieve at least one indexed recipe based on the at least one extended cooking ingredient and the at least one of cooking method preference and taste preference; and
   generate a recipe based on the at least one indexed recipe, the generated recipe being related to the at least one cooking ingredient and the at least one of cooking method preference and taste preference.

17. The apparatus of claim 14, the instructions further cause the one or more processors to:
   guide, based at least on the user's actions and/or cooking status of the at least one cooking ingredient, the user to cook following the recipe.

18. The apparatus of claim 13, wherein
   the diet intention indicates at least one of diet recommendation and product recommendation,
   the diet information includes at least one of food type, food name, dish name and concerned disease;
   the diet requirement includes health condition of the user; and
   the diet suggestion includes at least one of food name, dish name and product information.

19. The apparatus of claim 13, wherein
   the diet intention indicates diet knowledge acquirement;
   the diet information includes at least one of food type, food name, dish name and concerned disease;
   the diet requirement includes health condition of the user; and
   the diet suggestion includes diet knowledge.

* * * * *